United States Patent [19]

McMurchie

[11] Patent Number: 5,501,961
[45] Date of Patent: Mar. 26, 1996

[54] METHOD FOR DETECTION OF A PHYSIOLOGICAL ABNORMALITY

[75] Inventor: Edward J. McMurchie, Flagstaff Hill, Australia

[73] Assignee: Commonwealth Scientific and Industrial Research Organisation, Campbell, Australia

[21] Appl. No.: 977,431

[22] PCT Filed: Aug. 28, 1991

[86] PCT No.: PCT/AU91/00393

§ 371 Date: Feb. 26, 1993

§ 102(e) Date: Feb. 26, 1993

[87] PCT Pub. No.: WO92/3573

PCT Pub. Date: Mar. 5, 1992

[30] Foreign Application Priority Data

Aug. 28, 1990 [AU] Australia .............................. PK2017/90

[51] Int. Cl.$^6$ .............................. C12Q 1/06; G01N 33/48
[52] U.S. Cl. .................. 435/39; 435/26; 435/35; 435/810; 435/968; 436/503; 436/504; 436/56; 436/57; 436/63; 436/804; 436/808
[58] Field of Search ................................. 435/39, 26, 35, 435/810, 968, 975; 436/503, 504, 56, 57, 63, 804, 808

[56] References Cited

PUBLICATIONS

Cotton et al, *J. Clin. Invest.*, vol. 79, pp. 80–85, Jan. 1987.
Adragna et al, *Hypertension*, vol. 4, No. 6, pp. 795–804, 1982.
McMurchie et al. *Am. J. Clin. Nat.*, vol. 39, pp. 975–980, 1984.
Frelin et al, *J. Biol. Chem*, vol. 259, pp. 8880–8885, 1984.
Garay, (Suppl. I) *Hypertension*, vol. 10, No. 5, pp. I–11–I–14, Nov. 1987.
Mendoza et al, *Chemical Abstracts, vol. 108, p. 385, Ref. No. 52402a, 1987.*
Naccache et al, *Chemical Abstracts*, vol. 110, pp. 499, Ref. #55502k, 1988.
Akerman et al, *Chemical Abstracts*, vol. 117, p. 451, Ref. No. 107454n, 1992.
Abeywardena et al., Biochemical Pharmacology, vol. 33, No. 22, 15 Nov. 1984, pp. 3649–3654.
Greiff et al., Database WPI, Section Ch, Week 9129, Derwent Publications Ltd., London GB, Feb. 1991, Abstract, AN 91–209004.
Proc. West. Pharmacol. Soc., vol. 26, pp. 259–262 (1983).
Pflügers Arch.; vol. 411, pp. 606–612 (1988).
Pflügers Arch.; vol. 408, pp. 505–510, (1987).
Adragna et al, Hypertension, vol. 4, pp. 795–804, Nov./Dec. 1982.
Backcock et al, J.Chromatography, vol. 382, pp. 290–296 (1986).
Canali et al, Clin. Sci. (Suppl. 7), vol. 61, pp. 13s–15s (1981).
Canessa et al, New England Journal of Medicine, vol. 302, pp. 772–776, Apr. 1980.
S. J. Carr et al, J. Hypertension, vol. 8, pp. 139–146 (1990).
G. Clegg et al, The Lancet, No. 2, pp. 891–894 (Oct. 23, 1982).
D. Cusi et al, Clin. Sci. (Suppl. 7), vol. 61, pp. 33s–36s (1981).
J. M. Freiberg et al, Proc.Natl.Acad.Sci., vol. 79, pp. 4932–4936 (Aug. 1982).
C. Frelin et al, J. Biol. Chem., vol. 259, pp. 8880–8885 (1984).
Richardo P. Garay, Hypertension (Spll. I), vol. 10, No. 5, pp. I11–I14, (Nov. 1987).
S. A. Hilden et al, Am. J. Physiol, vol. 257, pp. F615–F622 (1989).
J. Kneisley et al, Clin. and Exper. Hyper.–Theory and Practice, vol. A12(5), pp. 693–708 (1990).
N. Lench et al, Lancet, vol. i, pp. 1356–1358 (1988).
Livne et al, Lancet, vol. 1, pp. 533–536 (Mar. 1987).
O. H. Lowry et al, J. Biol. Chem., vol. 193, pp. 265–275 (1951).
B. M. Margetts et al, Clin. Sci., vol. 69, pp. 165–175 (1985).
H. Meno et al, Mol. Cell. Cardiol., vol. 21, pp. 1179–1185 (1989).
McMurchie et al, Proc. Nut. Soc. of Aust., vol. 8, pp. 169–172 (1983).
McMurchie et al, Nut. Rep. Internat., vol. 29, pp. 519–526 (1983).
McMurchie et al, Am. J. Clin. Nut., vol. 39, pp. 975–980 (1984).
McMurchie et al, Comm. Health Sci., vol. 8, p. 272 (1984).
A. Moran et al, Biochem. Biophys. Res. Comm., vol. 163, pp. 269–275 (1989).
G. A. Morduchowicz et al, Kidney Int., vol. 36, pp. 576–581 (1989).
K. Morgan et al, Clin. Res., vol. 36, pp. 430 (Abstract).
L. L. Ng et al, J. Hypertension, vol. 7, pp. 471–475 (1989).
L. L. Ng et al, J. Hypertension, vol. 8, No. 6, pp. 533–537, (1990).
M. N. Orsenigo et al, BBA, vol. 1062, pp. 64–68 (1990).
S. M. Periyasamy et al, J. Biol. Chem., vol. 256, No. 11, pp. 6035–6041, (1990).
G. N. Pierce et al, Am. J. Physiol. (Heart Circ. Physiol. 27), vol. 258, pp. H255–H261.

(List continued on next page.)

*Primary Examiner*—Michael G. Wityshyn
*Assistant Examiner*—Abdel A. Mohamed
*Attorney, Agent, or Firm*—Birch, Stewart, Kolasch & Birch

[57] ABSTRACT

There is disclosed a method for the determination of a physiological abnormality in a human or animal subject, which method includes determining ion flux across the membrane of epithelial cells taken from the subject, wherein said cells are selected from the group consisting of check epithelial (buccal mucosal) cells, skin dermal epithelial cells and bladder epithelial cells. In one embodiment of the invention, the ion is a sodium ion, and the physiologically abnormality is hypertension or a predisposition towards hypertension.

39 Claims, 11 Drawing Sheets

OTHER PUBLICATIONS

K. Ramaswamy et al, BBA, vol. 981, pp. 193–199 (1989).

J. Sampugna et al, Lipids, vol. 23, pp. 131–136 (1988).

S. M. Seiler et al, J. Biol. Chem., vol. 260, pp. 4869–4876 (1985).

A. Semplicini et al, Am. J. Hypertension, vol. 2, pp. 903–908 (1989).

H. Tamai et al, Internat. J. Vit. Nutr., Res. 58, pp. 202–207 (1988).

M. Trevisan et al, Hypertension, vol. 5, No. 3, pp. 363–367 (1983).

S–L. Wang et al, FASEB Abstracts Part 1, No. 4, p. A324.

A. B. Weder et al, Hypertension, vol. 6, No. 1, pp. 116–123 (1984).

A. B. Weder et al, N. Eng. J. Med, vol. 314, No. 4, pp. 198–201 (1986).

M. Wehling et al, J. Hypertension, vol. 9, No. 6, pp. 519–524 (1991).

M. H. Weinberger et al, Hypertension, vol. 13, No. 3, pp. 206–212 (1989).

J. S. Wiley et al, Hypertension, vol. 6, No. 3, pp. 360–368 (1984).

R. R. Williams et al, J. Hypertension, vol. 8 (Suppl. 7), pp. S39–S46 (1990).

R. R. Williams et al, Clin. and Exper. Hyper.–Theory and Practice, vol. A12, No. 5, pp. 865–876.

R. R. Williams et al, Am. J. Epidemiol, vol. 118, pp. 338–344.

J. W. Woods et al, N. Engl. J. Med, vol. 306, No. 10, pp. 593–595 (1982).

L. Yap et al, J. Hypertension, vol. 7, No. 8, pp. 667–673 (1989).

J. A. Zadunaisky et al, Invest. Opthal. & Vis. Sci., vol. 30, No. 11, pp. 2332–2340, (1989).

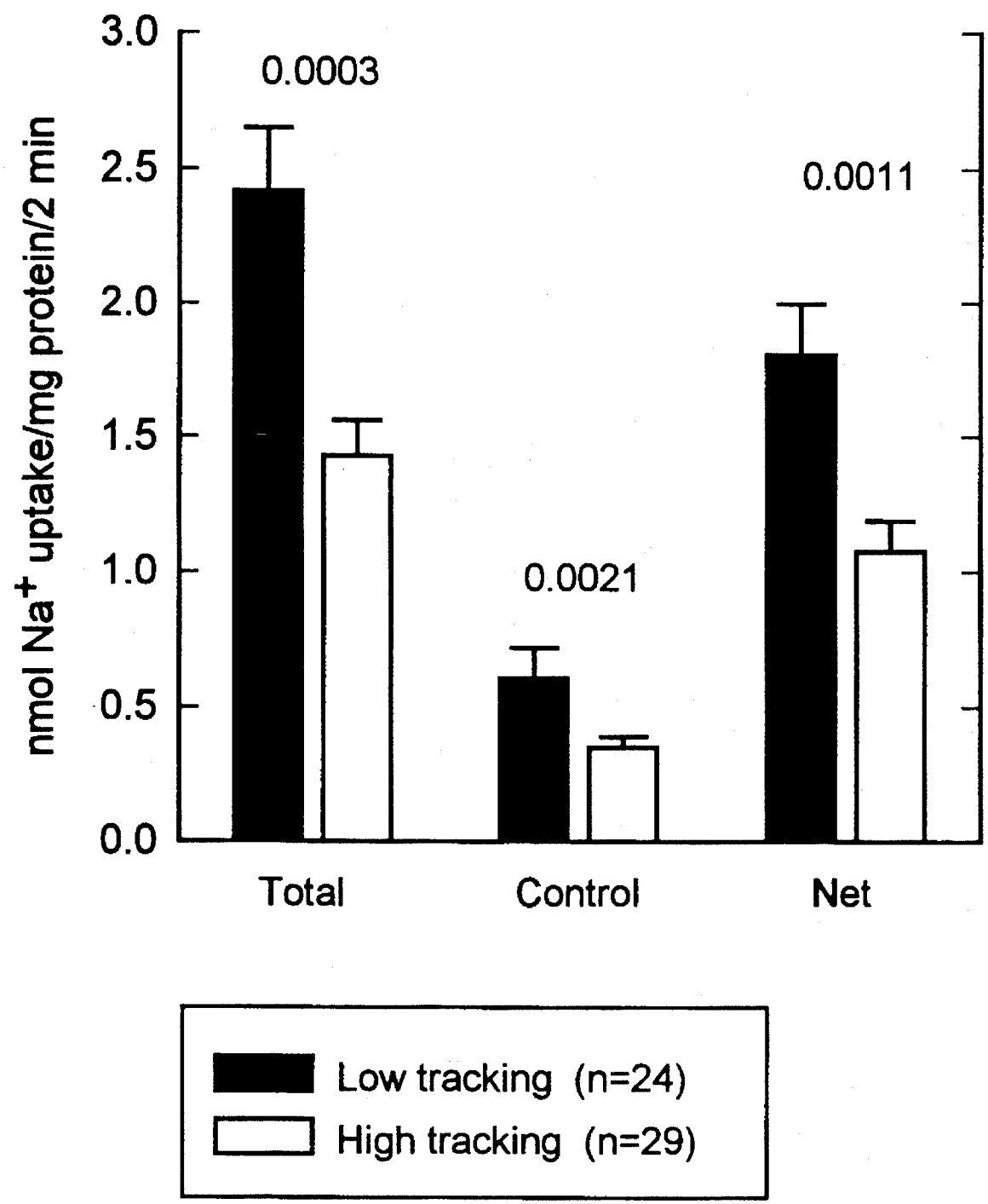

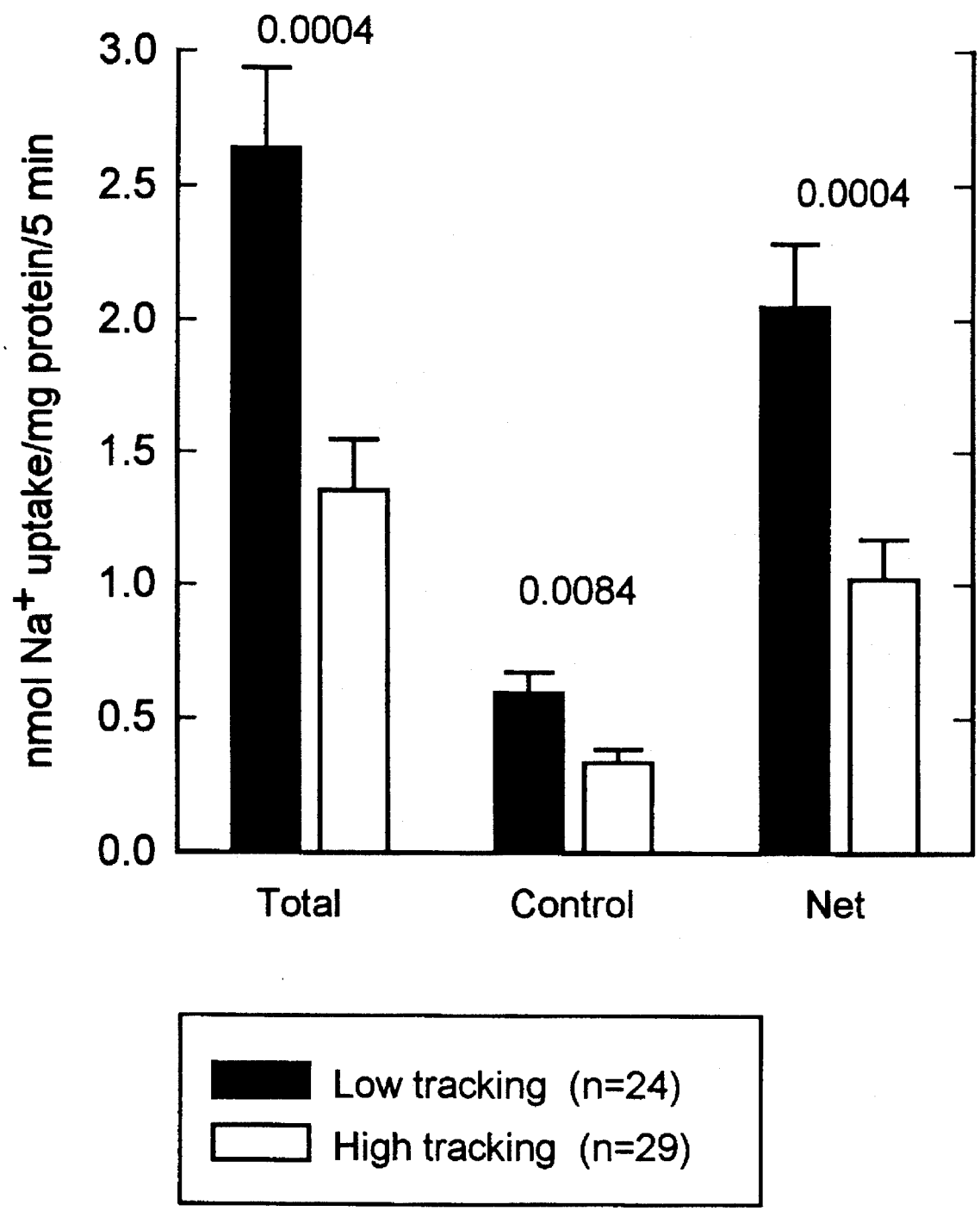

METHOD FOR DETECTION OF A PHYSIOLOGICAL ABNORMALITY

TECHNICAL FIELD

The present invention relates to an assay method for detecting a physiological abnormality such as hypertension in a human or animal, and to assays and kits for use in the method.

Hypertension is considered a major risk factor for heart disease. Untreated hypertension generally leads to irreversible damage to the heart and vasculature and undoubtedly shortens life. Cardiovascular problems associated with hypertension have decreased greatly during the last decade due to a combination of greater community awareness of the problem, early diagnosis by physical examination, and efficacious treatment of the condition once detected via the wide spectrum of antihypertensive medications currently on the market. In some cases hypertension can also be successfully contained by a combination of diet and lifestyle changes but the condition must be recognised and treated early if later deleterious effects are to be avoided. Nevertheless, the fact remains that hypertension is the commonest of the diseases affecting the heart and blood vessels.

Studies from the National Heart Foundation's Risk Factor Prevalence Study (1980) indicate that one in five men and one in six women in Australia have high blood pressure. By 50 years of age, 31% of men and 28% of women in Australia are hypertensive and by age 60 years this has increased to 47% and 39 % respectively. At present only about half of these persons are aware of their condition and only about one third are being successfully treated.

Most people suffering from the commonest variety of high blood pressure (essential hypertension which is of unknown aetiology), develop the disease in their thirties. However, during its early stages, it rarely produces symptoms. Unless a physical examination reveals that the blood pressure is high, a person may have the disease for many years without knowing. In general, they may be destined to develop hypertension at some time in the future due to their genetic predisposition. In terms of its inheritance, essential hypertension is understood to develop from a polygenic predisposition whose expression is enhanced by environmental mechanisms such as diet and whose outcome is fixed by inevitable structural changes due to the elevated blood pressure itself (Williams et at., 1990a,b).

The development of reliable detection techniques for the determination of physiological abnormalities such as the predisposition to hypertension is clearly of benefit in allowing early treatment. To date there is no satisfactory method to identify pre-hypertensive children; except perhaps, for the long-term procedure of blood pressure tracking. Standardised measurements of a child's blood pressure every two or three years during growth may show a consistently elevated pressure compared with other children of the same age, sex and body mass index and this will indicate a likelihood that the child will become a hypertensive adult. Blood pressure generally rises steadily with age and the blood pressure defined as mild hypertensive (95 mmHg diastolic and/or 150 mmHg systolic pressure) are rarely encountered in children. Nevertheless, the tendency to track in an upper or lower percentile rank is reasonably strong and is a good predictor of the adult ranking (Kneisley et at., 1990).

Clearly the development of a simple diagnostic test which is capable of detecting both the pre-hypertensive individual and those adults exhibiting labile blood pressure readings which make a definite diagnosis difficult, would herald a major breakthrough in early and definitive diagnosis and would allow for earlier treatment. Such a diagnostic test would be all the more acceptable if it had wide application such as in the testing of children of hypertensive parents. Furthermore, if the test is essentially non-invasive in its nature, it need not be confined to the above situations, but could be more wide reaching and applied to other "at-risk" groups in the community.

BACKGROUND ART

The most desirable form of test or predictive marker would be one which is indicative of some basic biochemical abnormality or defect in the hypertensive individual or in those individuals who would later develop hypertension, and which is likely to be related to the genetic predisposition of an individual to develop hypertension. Certainly no form of biochemical assay presently exists to detect those who may be predisposed to develop hypertension. Furthermore no biochemical test or assay has been developed which correlates unequivocally with all established hypertensive individuals. Existing biochemical assays appear to identify only certain subsets of hypertensives, i.e. only a certain proportion of hypertensive individuals display biochemical activities which are significantly different from the values determined for a comparable set of normotensive individuals (Garay, 1987). In this regard, the frequencies of $Na^+$ transport abnormalities in the red blood cells of Caucasian hypertensive subjects and the resulting change in the concentration of $Na^+$ in the red blood cell have revealed abnormalities in four major $Na^+$ transport pathways. However, as stated above, the extent to which these individual pathways are abnormal in hypertension is certainly not uniform, nor is the ability of these $Na^+$ transport abnormalities to discriminate between hypertensive and normotensive individuals, definitive. The maximal rate of red blood cell $Na^+$—$Li^+$ countertransport activity has been reported to be increased in only 20% to 50% of subjects in a hypertensive study group while that of the $(Na^++K^+)$ pump was increased in only 5% to 15% of the hypertensive group. An increased uptake of $Na^+$ into the red blood cell via a passive "leak" pathway was reported to be present in only 10% to 30% of hypertensive individuals (Garay, 1987). The above are clear examples of the failure of existing tests to clearly and totally discriminate between hypertensive and normotensive individuals. Furthermore, they do not address identification of the pre-hypertensive individual.

Existing tests developed by others rely on the measurement of $Na^+$, $Li^+$ or $H^+$ ion fluxes (whether singularly or in various combinations) across red blood cell, leucocyte or platelet cell membranes. Measurement of these ion fluxes have been done by direct means or indirectly by following cellular pH changes or swelling of a particular cell type. These tests have only been used in respect of adult subjects with established essential hypertension who have been compared with an appropriate control group of normotensive subjects who are matched for age, sex and body mass index. A complete list of these twenty or more studies are summarised in Table 6 and the full reference to each work is cited in the reference section. It must be pointed out that for some of these tests up to 120 ml of blood must be sampled in order to carry out such assays. Use of these tests in the case of pre-hypertensive subjects or with children has to our knowledge not been reported. The use of cheek cells in studies on existing hypertensives has also to our knowledge not been exploited by others.

DISCLOSURE OF THE INVENTION

It is an object of this invention to provide an alternative and more sensitive method for the determination of a physiological disorder such as essential hypertension in man. We have found that the presence of the above disorder may be reflected in the activity of a biochemical marker present in epithelial cells, the marker being the flow of ions, particularly $Na^+$ and $H^+$, across the membrane of the epithelial cell. This marker may be used to discriminate between subjects having the disorder and those who have not, such as has been done in an adult study group. Furthermore this marker may be used to discriminate between subjects who have yet to develop this disorder but are considered to be at the greatest risk of later developing hypertension due to the combination of blood pressure tracking characteristics and family history of hypertension, as has been done in an adolescent study group.

Accordingly, in a first aspect, the present invention provides a method for the determination of a physiological abnormality in a human or animal subject, which method includes determining ion flux across the membrane of isolated single epithelial cells taken from said subject.

The epithelial cell may be a skin dermal epithelial cell, a bladder epithelial cell (eg that contained in urine), a nasal epithelial-cell and the like. A particularly preferred cell is the cheek epithelial (buccal mucosal) cell.

In another aspect, the present invention provides an assay for use in the determination method of the invention said assay comprising determining the flux of a first ion across the membrane of epithelial cells under an imposed concentration gradient of a second ion.

The first and second ions may be cations. The first ion may be the sodium ion ($Na^+$), the second ion ($H^+$) and the epithelial cell such as the cheek epithelial (buccal mucosal) cell.

The invention will now be more particularly described in reference to the determination of hypertension and/or pre-disposition towards hypertension in humans.

The biochemical marker assayed for the determination of human hypertension (or pre-hypertension) is based on the rate of proton-dependent sodium ion ($Na^+$) uptake that occurs in epithelial cells such as cheek epithelial cells when measured as a function of the imposed proton gradient. It is likely, although not proven, that such activity is due in part to the $Na^+/H^+$ antiporter or exchanger which has been argued by others to be a component activity of the $Na^+/Li^+$ exchanger which is frequently measured in red blood cells and other cells derived from the blood in relation to hypertension (see Table 6).

Thus, in yet a further aspect, the present invention provides a method for the determination of hypertension and/or pre-disposition towards hypertension in a human subject, said method comprising the steps of:

establishing a proton ($H^+$) concentration gradient across the membrane of epithelial cells taken from said subject, the proton concentration being greater inside said cells than outside said cells; and determining the proton-dependent uptake of sodium ions ($Na^+$) by said cells when said cells are exposed to medium containing sodium ion ($Na^+$).

Preferably the cells are exposed to a medium containing a final concentration in the range 50 micromole to 150 millimole per liter $Na^+$. More preferably the cells are exposed to a medium containing a final concentration of about 1 millimole per liter $Na^+$.

The proton-dependent $Na^+$ transport may be determined directly by, for example, determining the uptake of radioactively labelled $Na^+$ (i.e. $^{22}Na^+$). It may also be determined indirectly by using a probe, such as a fluorescent probe specific for $Na^+$. Changes in proton-dependent $Na^+$ uptake could also be determined by measuring proton ($H^+$) movements across the cell membrane of an epithelial cell such as a cheek cell and the resulting pH changes inside the said cell either directly or indirectly; the latter method preferably using a fluorescent probe specific for pH.

The determination of $^{22}Na^+$ uptake may be performed at a number of proton gradients ranging from about 10:1 to 100:1 (inside→outside). Differences in the net rate of proton-dependent sodium ($Na^+$) transport in the cheek cell and the response of the $Na^+$ uptake activity of the cheek cell to the imposed proton gradient, may form the basis for discriminating the hypertensive (adult) and/or pre-hypertensive (adolescent) individual, from others in the study groups, as will be described.

Preferably, the epithelial cells are cheek epithelial cells, although other epithelial cells may be used as already indicated above. The advantages of using cheek cells are as follows:

1. Cheek cells are easily obtained from adults through to very young children and therefore the method suffers none of the problems inherent with blood sampling.

2. Cells can be obtained in a relatively non-invasive and entirely non-traumatic manner. Subjects may swish small amounts of water inside their mouth for a short period of time. The expectorate contains the "scuffed off" cheek cells.

3. A biochemical assay can be done on each individual as sufficient cells can be obtained from one person over a period of about 3 minutes following the procedure outlined above and fully detailed hereinafter.

As a result of the above points, the use of cheek cells in the method of the invention, would be expected to enjoy wide community acceptance in both general surveys and specific screening programs aimed at reducing the mortality and morbidity associated with hypertension.

In yet a further aspect, the present invention provides an assay kit for use in the method of the invention, said kit including an indicator for detection of ion concentration in a suitable container, and an inhibitor of $(Na^++K^+)$ATPase activity in a suitable container. The inhibitor may be ouabain. The indicator may be a fluorescent probe.

The assay kit for use in the method of the invention may also include an appropriate mix of organic phthalates in a suitable container. The organic phthalate mixture may be used in a rapid centrifugation procedure whereby epithelial cells could be spun out of their $^{22}Na^+$-containing uptake solutions into the mixture.

DETAILED DESCRIPTION OF THE ASSAY METHOD

In order to measure proton-dependent sodium transport it is necessary to subtract the background rate of non-proton dependent $Na^+$ uptake (passive diffusion) and to block the possible exit of $Na^+$ from the cheek cells by inhibiting $(Na^++K^+)$ATPase activity (the sodium pump). It is necessary also to have an accurate measurement of cell number preferably by using cell protein content from each subject, in order to compare activities of proton-dependent $Na^+$ transport occurring in cheek cells of different individuals.

The transport of $Na^+$ may be measured using radioactive sodium ions ($^{22}Na^+$) after cheek cells are either acidified by incubating in pH 5.5 buffer (for proton-dependent $^{22}Na^+$ uptake), or kept in pH 7.8 buffer (for non proton-dependent $^{22}Na^+$ uptake) and then added to media of differing pH values to provide a range of proton gradient values.

The proton-dependent and non-proton dependent rates of $^{22}Na^+$ transport into cheek epithelial cells may be measured over various time points from as short as 15 seconds to as long as 40 minutes incubation at 25° C. For the study on adult hypertensive subjects to be described, uptake of $^{22}Na^+$ was determined at 30 seconds and 5 minutes, while for the adolescent study to be describe, uptake of $^{22}Na^+$ was determined at 2 minutes and 5 minutes incubation. The uptake reaction is terminated and the cells containing $^{22}Na^+$ are collected by rapid filtration using 0.45 micron Millipore filters. Trapped $^{22}Na^+$ is counted by beta-liquid scintillation counting and the rates of $^{22}Na^+$ uptake are compared on a milligram cell protein basis having determined cell protein content by the method of Lowry et al., (1951).

A full description of the methods used for the recruitment of subjects for each of the studies described herein, the method of collection of the cheek epithelial cells, the method of measuring the $Na^+$ transport by the $Na^+/H^+$ antiporter assay, the composition of all solutions pertinent to the said assay, the source of all chemicals and the methods used for the analysis of dam, are given hereinafter.

The present invention will now be described in reference to the accompanying figures. It is understood that various other modifications and/or alterations may be made without departing from the spirit of the present invention as it is outlined below.

BRIEF DESCRIPTION OF THE DRAWINGS

FIG. 6 illustrates sodium transport rates in cheek cells of low BP and high BP tracking adolescents (2 min incubation). Proton dependent (total), non proton dependent (control) and net proton·dependent (total minus control) rates of $^{22}Na^+$ uptake in cheek cells at a proton gradient (inside→outside) of 100:1 were determined as described in Testing Method 3.

FIG. 7 illustrates sodium transport rates in cheek cells of low BP and high BP tracking adolescents (5 min inculbation). Proton dependent (total), non proton dependent (control) and net proton dependent (total minus control) rates of $^{22}Na^+$ uptake in cheek cells at a proton gradient (inside→outside) of 100:1 were determined as described in Testing Method 3.

CHARACTERISATION OF HUMAN CHEEK CELL SODIUM ION (NA$^+$) TRANSPORT: (NA$^+$/H$^+$ ANTIPORTER ASSAY)

The method of the invention in its preferred form relies on the fact that human cheek cells display significant sodium transport activity which by several criteria appears to be primarily due to the $Na^+/H^+$ antiporter system. Although the $Na^+/H^+$ antiporter system is known to be present in many mammalian cell types (see full reference list relating to Table 5), to our knowledge, there has been no reports in the scientific or patent literature that human cheek cells possess this activity. It therefore follows that the application of such a finding to the detection of a physiological abnormality such as the identification by biochemical means, of hypertensive and/or prehypertensive individuals is also unique.

Figure 1:
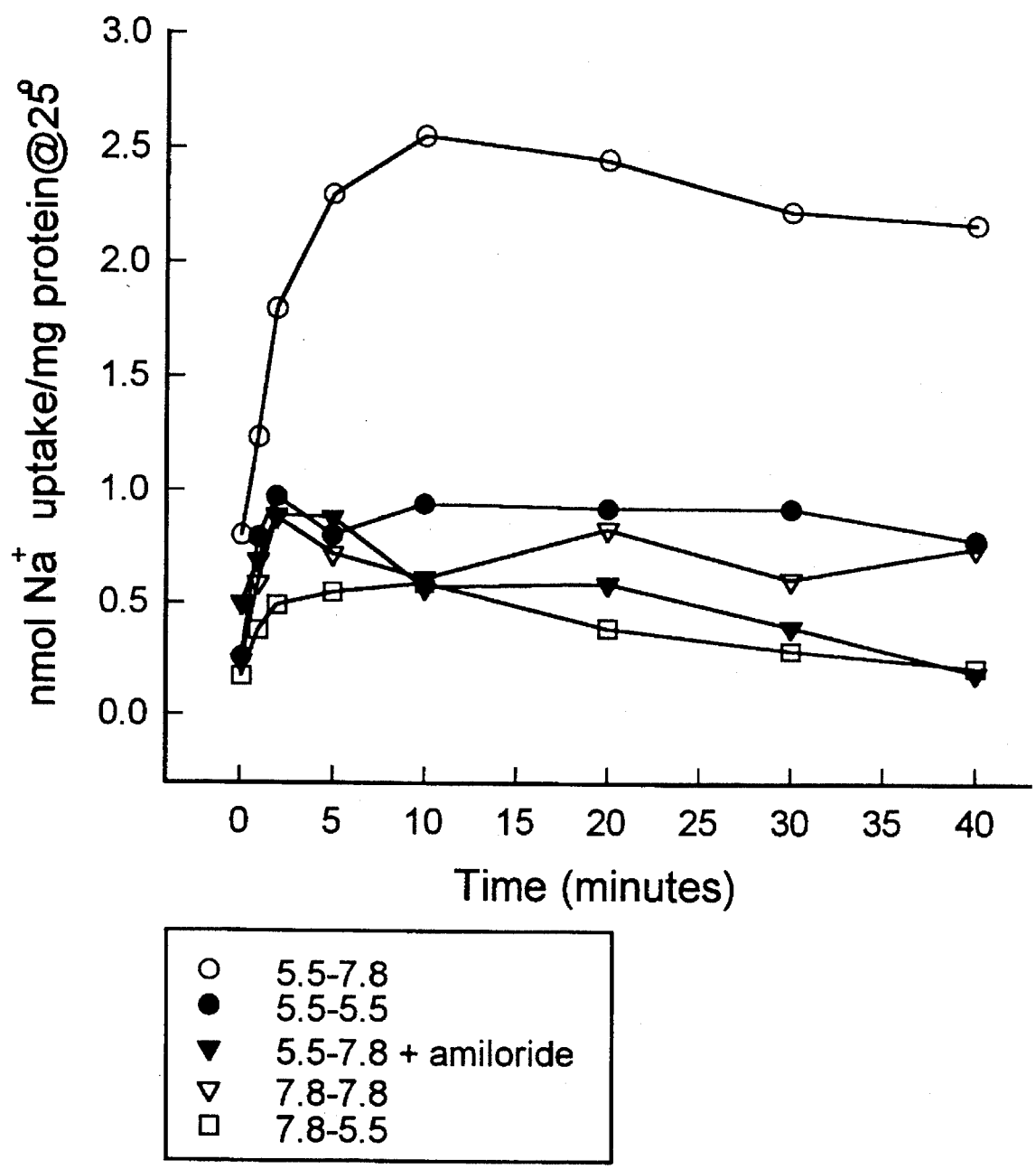
FIG. 1 illustrates the time course for sodium transport activity in cheek cells of a normotensive adult. The graph shows proton dependent and non-proton dependent rates at $^{22}Na^+$ transport in cheek cells determined at indicated pH values (inside→outside) over a period of 40 minutes at 25° C., using the methods fully described in Appendix 1. Amiloride at a final concentration of 1 mM was tested at a proton gradient of 100:1

Human cheek cells display significant sodium transport (Na$^+$ uptake) activity, and, as a result of the various conditions tested in FIG. 1, this activity is characteristic of Na$^+$ uptake via the Na$^+$/H$^+$ antiporter system. The data shown in FIG. 1, which is derived using the methods fully described in Testing Method 1, shows that greatest Na$^+$ uptake occurs when cells are acidified at a pH of 5.5 and then Na$^+$ uptake is allowed to occur in pH 7.8 media. Under these conditions, this transient 100:1 outwardly-directed proton (H$^+$) gradient leads to significant Na$^+$ uptake (as measured by $^{22}$Na$^+$). Uptake of Na$^+$ is greatly reduced when no proton gradient exists, e.g. pH $5.5_{inside} \rightarrow 5.5_{outside}$ and pH $7.8_{inside} \rightarrow 7.8_{outside}$, or when an inwardly-directed proton gradient exists, e.g. pH $7.8_{inside} \rightarrow 5.5_{outside}$. This data strongly infers that Na$^+$ uptake is directly coupled to proton efflux and, as such, implies that the Na$^+$/H$^+$ antiporter system can be activated in human cheek cells by the methods described.

As will be shown hereafter, cheek cell Na$^+$ transport is also a function of the magnitude of the imposed (outwardly-directed) proton gradient, with the amount of Na$^+$ uptake generally increasing when the proton gradient is increased. (It is this response however which differs between the study groups investigated and forms part of the present invention). Nevertheless, this direct relationship between the magnitude of the proton gradient and the magnitude of the Na$^+$ uptake, further implicates the presence of Na$^+$/H$^+$ antiporter activity in human cheek cells.

Further evidence linking Na$^+$ transport activity in the cheek cell to Na$^+$/H$^+$ antiporter activity, is provided by the results obtained with the specific Na$^+$/H$^+$ antiporter inhibitor, amiloride. As is shown in FIG. 1, addition of 1 mM amiloride to cheek cells activated to have a 100:1 outwardly-directed proton gradient, reduces Na$^+$ transport activity to levels comparable to that observed in cheek cells where no proton gradient exists.

Two other characteristics of cheek cell Na$^+$ transport are evident from FIG. 1. A steady-state level of Na$^+$ uptake is reached after about 10 minutes (probably corresponding in time to the full dissipation of the proton gradient), and an "overshoot" or decrease in the rate of the Na$^+$ uptake occurs after that time. Both of these observations are characteristic of the profile of Na$^+$/H$^+$ antiporter activity obtained in other cell types (see for examples references in Table 5) and further implicates the Na$^+$/H$^+$ antiporter as being the predominant system involved in Na$^+$ transport in the human cheek cell.

The assay conditions for determining cheek cell Na$^+$ transport activity which were routinely used in the studies to validate this invention, are modified from existing methods for assaying Na$^+$/H$^+$ antiporter activity present in other tissues and cell types (as indicated in Testing Method 1). Our modifications are based on empirical observations using cheek cells which were made during the early course of the studies described herein, and no attempt is made to exhaustively investigate all the characteristics of human cheek cell Na$^+$ transport and the role of the Na$^+$/H$^+$ antiporter in this transport system. Not withstanding this, the following observations have been made with respect to Na$^+$ transport and Na$^+$/H$^+$ antiporter activities in human cheek cells, and these have hitherto not been previously reported:

Rates of Na$^+$ uptake by human cheek cells are comparable to the reported rates of Na$^+$ uptake (via the Na$^+$/H$^+$ antiporter system) in other cell and tissue types as outlined in Table 5, even when allowance is made for the wide variety of assay methods employed in the various studies listed.

The final concentration of Na$^+$ in all the cheek cell assays described n this invention, is 1 mM. As such, this concentration is well below the K$_m$ (Michaelis-Menton constant) for the cheek cell Na$^+$/H$^+$ antiporter system which is between 6 mM and 10 mM Na$^+$ for a normotensive adult subject.

The K$_m$ for the internal proton binding site of the Na$^+$/H$^+$ antiporter of cheek cells from a normotensive adult subject is about 1.7 μM (H$^+$). The Hill coefficient of this site approximates 1.

Cheek cell Na$^+$/H$^+$ antiporter activity is not greatly affected by the K$^+$ ionophore, valinomycin, indicating that cell membrane potential does not greatly influence Na$^+$ transport activity. As such, this is in agreement with the findings reported in the scientific literature for Na$^+$/H$^+$ antiporter activity in other cell and tissue types.

The extent of Na$^+$ transport in cheek cells having an outwardly-directed proton gradient of 100:1, is many fold higher in the presence of the ionophores monensin (Na$^+$:H$^+$) or nigericin (K$^+$: H$^+$). Such findings also validate the existence of Na$^+$/H$^+$ antiporter activity in human cheek cells.

The transport of Na$^+$ into cheek cells following the activation of the Na$^+$/H$^+$ antiporter system by an outwardly-directed proton gradient, represents the net transport of the Na$^+$ ions, which is, in turn, the sum of the rate of Na$^+$ uptake and the rate of Na$^+$ efflux. Efflux of Na$^+$ from the cheek cell occurs simultaneously to, and is dependent on, the activation of the Na$^+$/H$^+$ antiporter system and the resulting increase in cheek cell $^{22}$Na$^+$ content. However, up to a time of 10 minutes, Na$^+$ influx exceeds Na$^+$ efflux. The rate of Na$^+$ efflux is also time-dependent and hence dependent on the extent of uptake of Na$^+$ into the cheek cell which has occurred via the Na$^+$/H$^+$ antiporter. The "overshoot" phenomenon mentioned previously, may represent a situation of greater Na$^+$ efflux than influx after complete dissipation of the proton gradient and subsequent deactivation of the Na$^+$/H$^+$ antiporter activity.

The contribution of other known Na$^+$ transport systems to the net transport of Na$^+$ in human cheek cells is not great. Efflux of (transported) $^{22}$Na$^+$ out of the cheek cell via the Na$^+$+K$^+$-ATPase (sodium pump), does affect the net rate of Na$^+$ influx to a small but significant extent (see FIG. 2). However, to entirely eliminate any contribution by this Na$^+$ transport pathway to net cheek cell Na$^+$ transport activity, 1 mM ouabain, a specific inhibitor of the sodium pump, is routinely included in all those assays concerned with the studies that validate this invention (as indicated in Testing Methods 2–3). On the basis of inhibitor studies using bumetanide and frusemide, the contribution of the Na$^+$/K$^+$/2Cl$^-$ cotransport system to the overall Na$^+$ transport activity of human cheek cells, is insignificant.

Human cheek cells also contain a significant level of Na$^+$/Li$^+$ antiport activity in which Na$^+$ uptake into cells is coupled to an outwardly directed Li$^+$ gradient.

In conclusion, the Na$^+$ transport activity of human cheek cells, which is used to validate this invention, has only partly been characterised at the biochemical level. However it is now firmly established that the Na$^+$/H$^+$ antiporter system is largely responsible for the observed Na$^+$ transport. All the abovementioned characteristics of Na$^+$ transport in human cheek cells therefore represent new and unique findings not previously published in the scientific or patent literature.

The discovery of the potential for human cheek cells to transport Na$^+$ in a predictable manner, forms the basis for the conclusion that hypertensive and prehypertensive individuals can be identified using a biochemical marker. These specific details of the invention will now be described.

Adult Cheek Cell Study

Subjects used in this study were recruited from adult volunteers identified following several blood pressure screening programs. None of the control or hypertensive subjects were receiving anti-hypertensive medication at the time of the blood pressure screening or sampling of cheek cells. All measurements were done using a Dinamap (automatic blood pressure recording instrument). Those first identified as being mildly hypertensive (diastolic blood pressure $\geq 95$ mm Hg), were subsequently re-measured over a period of several days to confrim the reading. Systolic and diastolic blood pressures, age and gender of the two groups used in this example are shown in Table 1. Systolic and diastolic blood pressures were significantly different between the two groups, while the groups were well matched for age and gender, although the hypertensive group exhibited a slightly greater body mass index (BMI).

in which $Na^+/H^+$ antiporter activity has not been activated by a proton gradient), is also much lower than that for the normotensive study group, but statistical significance is not achieved.

Figure 3:
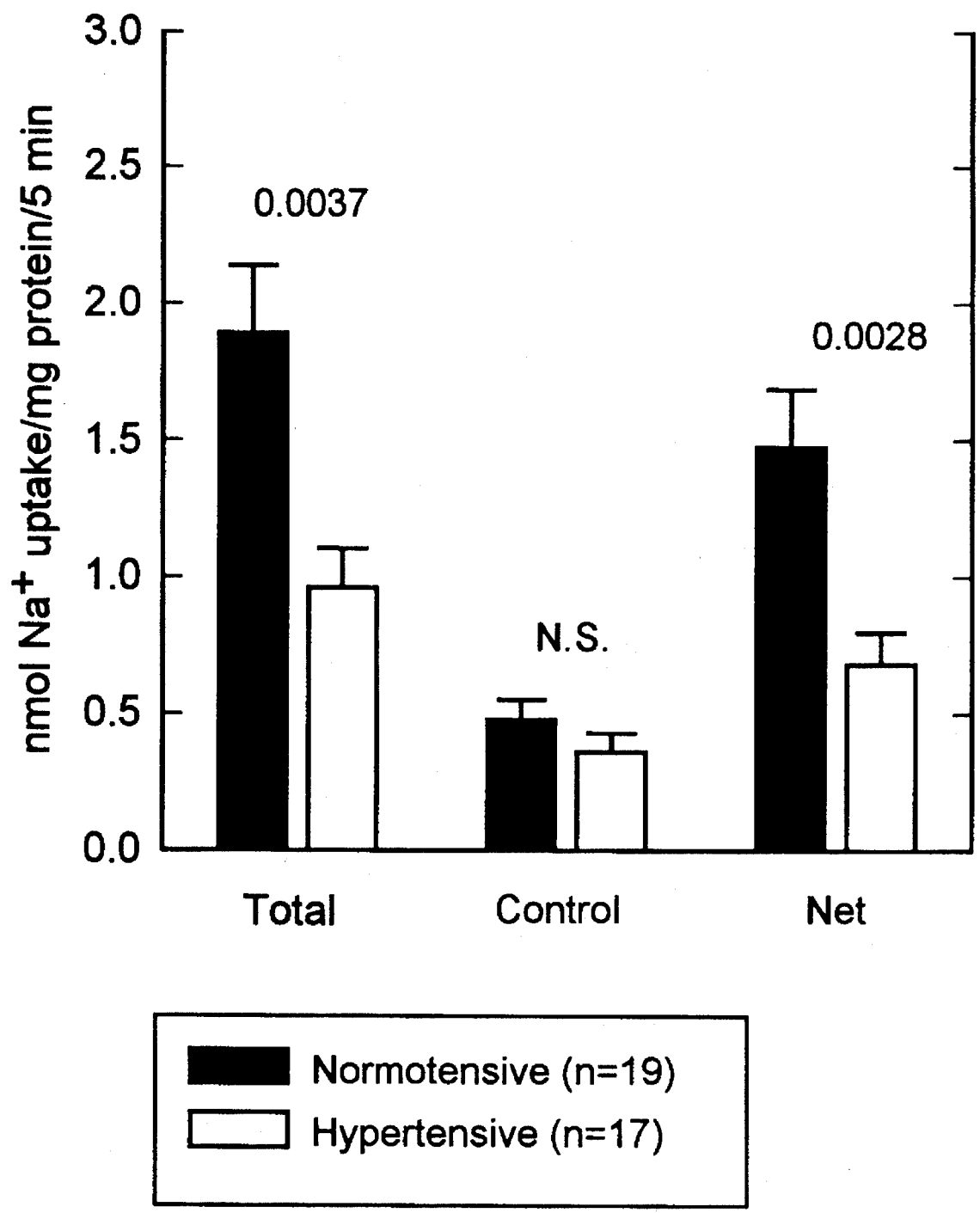
FIG. 3 illustrates sodium transport in cheek cells of normotensive and hypertensive adults (5 min incubation). Proton dependent (total), non proton dependent (control) and net proton dependent (total minus control) rates of $^{22}Na^+$ uptake in cheek cells all, with 1 mM ouabain, were determined as described in Testing Method 2.

FIG. 3 compares $Na^+$ transport in cheek cells of normotensive and hypertensive adult study groups after the $Na^+$ transport assay has been allowed to proceed for 5 minutes. It is clear that the total and the net rates of $Na^+$ uptake for the hypertensive study group are only about 50% of that evident for the normotensive study group. Furthermore, this difference in the (proton-dependent) $Na^+$ uptake rates is highly significant between the two study groups. The control (non-proton dependent rate) of $Na^+$ uptake is not significantly different between the study groups.

The difference in cheek cell $Na^+$ transport activity between normotensive and hypertensive study groups is

TABLE 1

CHARACTERISTICS OF NORMOTENSIVE AND HYPERTENSIVE SUBJECTS USED IN THE CHEEK CELL ASSAY FOR HUMAN HYPERTENSION

| | | BLOOD PRESSURE | | | | | |
|---|---|---|---|---|---|---|---|
| | (n) | SYSTOLIC (mm Hg) | DIASTOLIC (mm Hg) | AGE (years) | M/F | % F | BMI (Kg/m$^2$) |
| Normotensive | 19 | $129 \pm 2$[1] | $73 \pm 2$ | $47 \pm 2$ | 13/6 | 31.5 | $23.4 \pm 0.8$ |
| Hypertensive | 17 | $166 \pm 5$ | $101 \pm 2$ | $49 \pm 2$ | 12/5 | 29.4 | $25.9 \pm 1.0$ |
| | 15[2] | $168 \pm 5$ | $102 \pm 2$ | $50 \pm 2$ | 10/5 | 33.3 | $26.0 \pm 1.0$ |
| Significance | | P < 0.0001 | P < 0.0001 | N.S. | — | — | P < 0.05 |

[1] Data is presented as the mean ± SEM for the indicated number of subjects (n) in each group. Differences between means were determined by Student's unpaired t-test significant.
[2] For proton gradients performed at 19:1, 40:1 and 75:1.

Cheek cells were isolated from all subjects in the morning and assayed in the afternoon of the same day as collection. Proton-dependent sodium transport was determined using triplicate assays of both the total sodium uptake rate and the non proton dependent rate to determine the proton-dependent sodium uptake rate, as described in the appropriate methods of Testing Method 2. The variability of the measurements across all assay conditions for any one individual averaged 6.2% (interassay variation), while for assays on the same subject(s) performed on different days, the variability averaged 10.6% (intra-individual variation).

Figure 2:
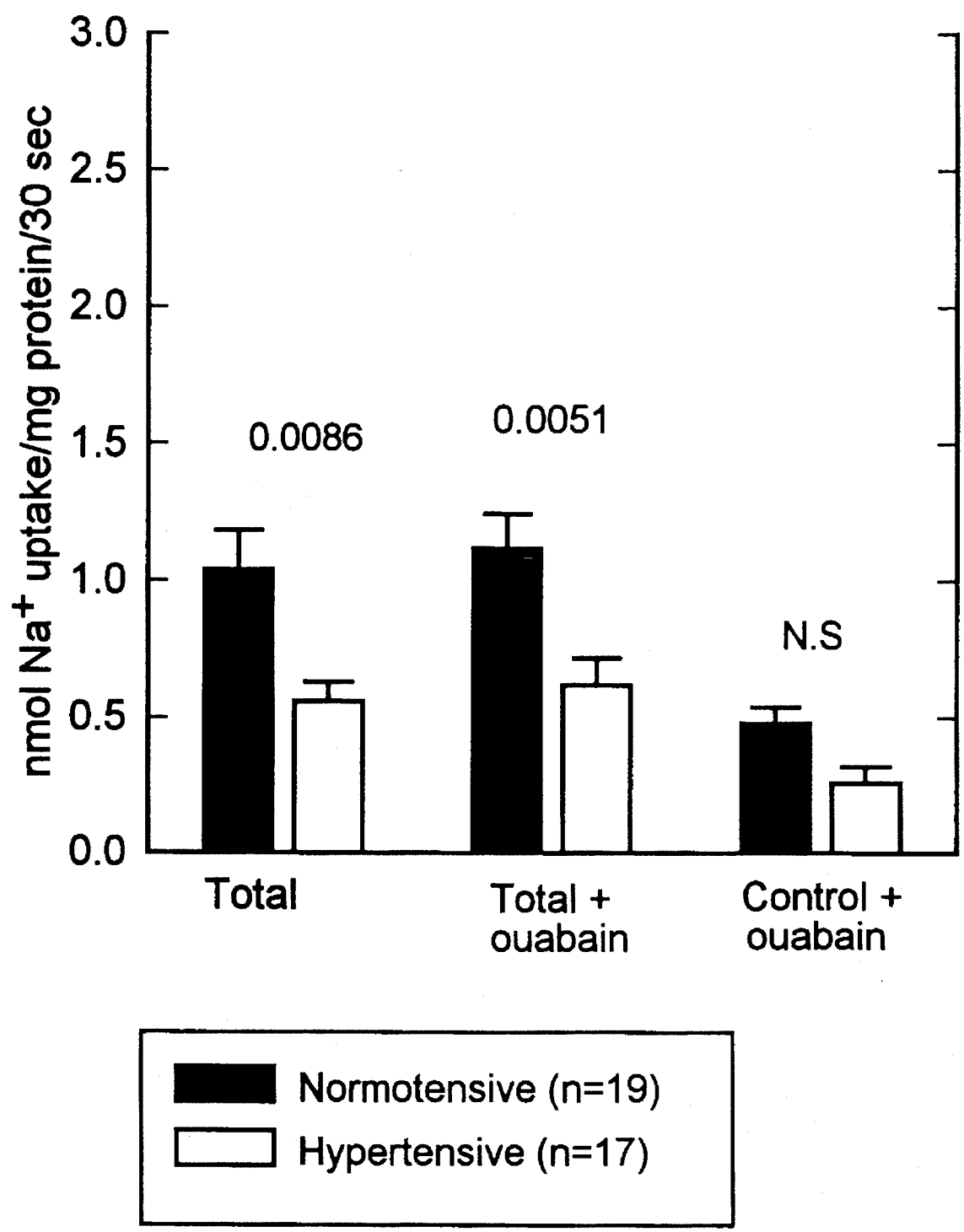
FIG. 2 illustrates proton dependent (total), proton dependent+ouabain and non proton dependent (+ouabain) sodium transport rates in cheek cells of normotensive and hypertensive adults (30 sec incubation). Rates of $^{22}Na^+$ uptake in cheek cells at a proton gradient (inside→outside) of 100:1 were determined as described below in Testing Method 2.

FIG. 2 compares $Na^+$ transport in cheek cells of normotensive and hypertensive adult study groups after the $Na^+$ transport assay has been allowed to proceed for 30 seconds. As indicated in the legend to this figure, the total rate of $Na^+$ uptake is that observed when an outwardly-directed proton gradient of 100:1 is applied to cheek cells. Inclusion of 1 mM ouabain, a specific inhibitor of $(Na^+ + K^+)$-ATPase activity, results in a small increase in $Na^+$ uptake in both normotensive and hypertensive adult subjects. As discussed in the previous section, this result suggests that the contribution of the sodium pump to $Na^+$ efflux, is minimal. Ouabain (at 1 mM) is added to all assays in which $Na^+$ transport activity of adults and adolescent study groups is investigated to completely negate any contribution from the sodium pump. It is also clearly apparent from FIG. 2, that the total and total plus ouabain rates of $Na^+$ uptake in cheek cells of the adult hypertensive study group is only about 50% of that evident in cheek cells from the normotensive study group. Furthermore, this difference in $Na^+$ uptake rates for the above conditions is highly significant between the two study groups. For hypertensive adult subjects, the control rate of $Na^+$ uptake in the presence of ouabain, (which represents the rate of "passive" $Na^+$ uptake into cheek cells clearly apparent only under conditions which would lead to activation of the $Na^+/H^+$ antiporter system, i.e. the presence of an outwardly-directed proton gradient. This fact indicates that intrinsic differences in the activity of the $Na^+/H^+$ antiporter system and/or its activation by a proton gradient, may underlie the dramatic difference seen in the $Na^+$ transport activity between the normotensive and the hypertensive study groups. This has been further investigated in cheek cells obtained from the respective adult study groups, by comparing the response of the $Na^+/H^+$ antiporter system (and hence $Na^+$ uptake), to outwardly-directed proton gradients which differ in their magnitude.

Figure 4:
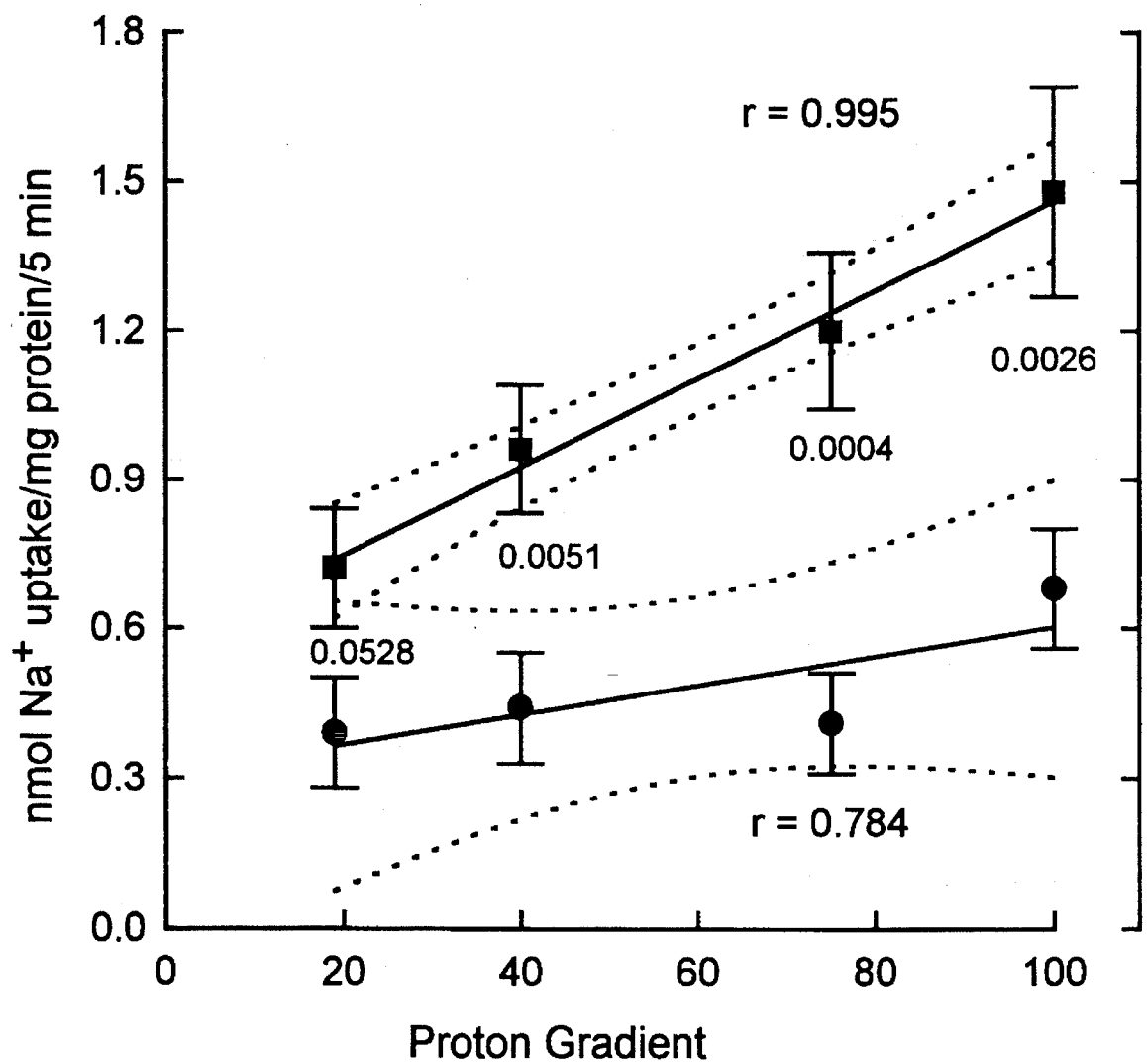
FIG. 4 illustrates the effect of altered proton gradient on the net rate of proton dependent sodium transport in cheek cells of normotensive and hypertensive adults. Net rates of proton dependent (total minus control) $^{22}Na^+$ transport at 5 minutes were determined at the indicated proton gradient (inside→outside) values as described in Testing Method 2. Values for the regression coefficient (r) and the 95% limits of confidence for each group are indicated. For the normotensive adult group, n=19 subjects were used for each proton gradient value. For the hypertensive adult group (n) values at each proton gradient were 17 (19:1); 15 (40:1); 15 (75:1) and 17 (100:1).

The response of cheek cell proton-dependent sodium transport to proton gradients varying in magnitude from 19:1 to 100:1 (inside→outside) in the normotensive and hypertensive study groups is shown in FIG. 4. A clear distinction is apparent between the two groups. Not only is the rate of proton-dependent sodium transport in the hypertensive subjects markedly reduced at all proton gradient values as compared to the normotensive group, but for the hypertensives, the rate of proton-dependent sodium transport is unaffected by a change in proton gradient values from 19:1 to 75:1. Only at a proton gradient value of 100:1 does the rate of proton-dependent sodium transport of the hypertensive group increase above the value exhibited for proton gradient values of 19:1, 40:1 and 75:1. The difference in the rate between the two groups is extremely significant for all but the 19:1 value of the proton gradient.

Figure 5:
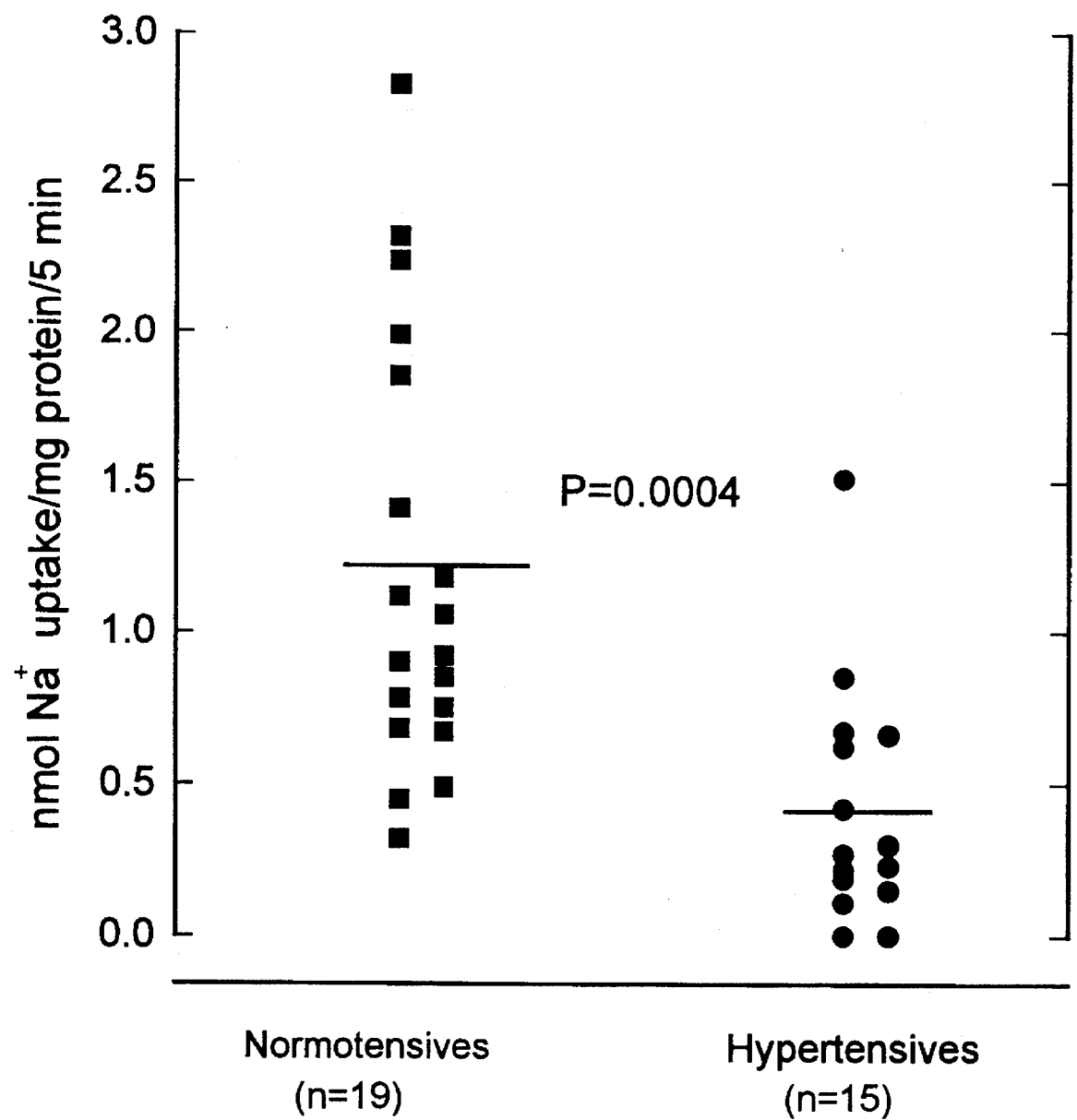
FIG. 5 illustrates sodium transport rates in cheek cells of normotensive and hypertensive adults. Net rates of proton dependent a $^{22}Na^+$ transport (total minus control) at 5 minutes incubation at a proton gradient value (inside→outside) of 75:1 were determined as described in Testing Method 2.

The rate of proton-dependent sodium transport in cheek cells as a result of imposing a proton gradient of 75:1 (inside→outside) for 15 individual hypertensives and 19 normotensive subjects, is shown in FIG. 5. [A proton gradient of 75:1 refers to the ratio between the hydrogen ion concentration in the cell loading buffer and the assay (uptake buffer) respectively, after taking into account the dilution effects arising as a result of the manner in which the transport assay is performed. For a 75:1 proton gradient to be achieved, the cell loading buffer has a value of pH 5.5 and the assay uptake buffer a value of pH 7.65]. Cheek cells from the 15 hypertensive subjects display a markedly reduced mean rate of proton-dependent sodium transport (mean±SEM; 0.41±0.1 nmol $Na^+$.mg protein.5 min) which is 34% of the rate for the 19 normotensive subjects (1.20±0.16 nmol $Na^+$.mg protein.5 min), and this difference is highly significant (P=0.0004; Student's unpaired t-test). Some overlap between the values for hypertensive and normotensive subjects is apparent in this data (approximately 6% as defined in Table 6). However as discussed in relation to Table 6, this degree of overlap is less than that obtained in any previous study where the rates of cation transport in other cell types have been measured in relation to hypertension.

The response of cheek cell proton-dependent sodium transport to a change in the value of the proton gradient from 19:1 to 75:1, is shown in Table 2. These values represent the slope of the line between the abovementioned proton gradient values as depicted in FIG. 4. As can be seen from this table, the slope of the line between the normotensive and hypertensive subjects differs by a factor of 24 fold at a significance level of P=0.0028; i.e. the mean increase in proton-dependent $^{22}Na^+$ transport is 24 times greater in the normotensive subjects as compared to the hypertensive subjects. For the above parameter of proton-dependent sodium transport, the extent of overlap between the values for the individual normotensive and hypertensive subjects is 11.5% as defined in Table 6.

TABLE 2

RESPONSE OF CHEEK CELL PROTON-DEPENDENT SODIUM TRANSPORT TO A CHANGE IN THE PROTON GRADIENT IN NORMOTENSIVE AND HYPERTENSIVE ADULT SUBJECTS

| Normotensive | n = 19 | 0.48 ± 0.1[1] | nmol $^{22}Na$ · mg protein · 5 min (for a change in the proton gradient from 19:1 to 75:1) |
|---|---|---|---|
| Hypertensive | n = 15 | 0.02 ± 0.1 | |
| Significance | | P = 0.0028 | |

[1]Data is presented as the mean ± SEM for the indicated number of subjects (n) in each group. The significance of the difference between the mean was determined by Student's unpaired t-test.

The present invention has significant potential in the determination of human hypertension. Marked differences in the rate of proton-dependent $^{22}Na^+$ transport into cheek cells are apparent between age and sex-matched hypertensives and normotensive subjects under a wide range of assay conditions. However when the assay is performed at a proton gradient value of 75:1 and measured over a period of 5 minutes, the differences between normotensive and hypertensive subjects is most pronounced, (mean value of proton-dependent $^{22}Na^+$ uptake in the hypertensive group is only 33% of that evident in normotensive group); of highest statistical significance, (P value of 0.0004 between the two groups, i.e. 1 chance in 2,500 that the result occurred by chance alone); and capable of the greatest discrimination between the two groups (i.e. where least overlap occurs; average 6% as defined in Table 6. The increase in the rate and amount of proton-dependent $^{22}Na^+$ uptake when the proton gradient is increased from a value of 19:1 to 75:1 is also a useful parameter to discriminate between hypertensive and normotensive subjects.

Adolescent cheek cell study

The preceding sections have clearly demonstrated that:

1. Human cheek cells have the ability to transport $Na^+$ primarily via proton gradient activation of an associated $Na^+/H^+$ antiporter system;

2. Them is a statistically significant reduction in the magnitude of $Na^+$ transport activity in cheek cells from adult hypertensive subjects compared to adult normotensive subjects;

3. The difference in $Na^+$ transport activity between these adult study groups appears related to the proton-gradient dependent cheek cell $Na^+/H^+$ antiporter system.

In order to extend these findings and test one of the claims of this invention, i.e. that the biochemical parameter under study viz-a-viz $Na^+$ transport in cheek cells, can be used to identify pre-hypertensive individuals, a study using adolescents is described.

Full details of the methods used in the Adolescent cheek cell study are described in Testing Method 3. Based on the previously reported finding that the tendency during childhood for blood pressure to track in an upper or lower percentile is reasonably strong, and that it is a good predictor of the adult ranking, adolescents who consistently tracked in an upper and lower percentile rank, were identified from blood pressure readings taken over a period of at least four years. Details of those adolescents who were finally selected for this study are described in Table 3. The low blood pressure (BP) tracking group of n=24, represents 4.8% of the total group of n=504 adolescents who were screened. Subjects within this group consistently exhibited the lowest systolic BP reading from the commencement of the study in 1986 to the time at which cheek cell $Na^+$ transport activity was determined. In contrast, the high BP tracking group, representing 5.7% of the total group screened, consistently exhibited the highest (systolic) BP readings of all the subjects screened. (Statistical procedures used to determine the BP ranking status of these two groups of adolescents are fully described in Testing Method 3). It can be clearly seen from the data in Table 3, that the difference in the systolic BP between the two adolescent groups remained significantly different (P<0.0001) over the four-year period of the tracking study. No significant difference in the age or BMI of the two groups is evident at the time the cheek cells were actually sampled. However, of particular importance is the extent by which the two adolescent groups differ in their incidence of a definitive family history of hypertension. In the high BP tracking group, 7 of the 29 subjects (24%) had a definitive family history of hypertension with one or both of the parents being treated with a recognised anti-hypertensive medication. This contrasts with the low BP tracking group where a transient secondary hypertension (eclampsia) was evident for the mother of one of the subjects. A higher proportion of males (69%) is present in the high BP tracking group in comparison to the low BP tracking group, in which 50% were male.

TABLE 3

COMPARISON OF LOW BP TRACKING AND HIGH BP TRACKING SUBJECTS USED IN THE CHEEK CELL STUDY OF SODIUM TRANSPORT IN ADOLESCENTS

| 1990–1991 | LOW BP TRACKING | HIGH BP TRACKING | P | (H–L) Δ |
|---|---|---|---|---|
| (n) | 24 (4.8%) | 29 (5.7%) | — | |
| M/F | 12/12 | 20/9 | | |
| AGE | 16.5 ± 0.13 | 16.6 ± 0.14 | NS | 0 |
| BMI (Kg/m$^2$) | 20.8 ± 0.8 | 22.9 ± 0.7 | NS | 2.1 |
| SYSTOLIC BP (1990–91) | 108 ± 1.1 | 128 ± 1.3 | <0.0001 | 20 mm Hg |
| DIASTOLIC BP (1990–91) | 58 ± 1.2 | 63 ± 1.8 | <0.008 | 5 mm Hg |
| FAMILY HISTORY 1st generation | 1 (eclampsia) | 7 (24%) | | |
| SYSTOLIC BP (1986–87) | 100 ± 0.7 | 123 ± 0.8 | <0.0001 | 23 mm Hg |
| SYSTOLIC BP (1989–90) | 105 ± 0.9 | 129 ± 1.0 | <0.0001 | 24 mm Hg |

(NS) Not significant

It must be emphasised that these groups are not directly comparable to the normotensive and hypertensive adult study groups referred to in the previous section. For example, none of the high BP tracking adolescents recorded BP readings which impinged on values characteristic of mildly adult hypertensive subjects. However, each group displayed consistently different BP tracking behaviour over a period of 4 years up to the time of cheek cell sampling. As such, it would be expected that a far greater proportion of those subjects within the high BP tracking group may later develop hypertension compared to the low BP tracking group. This prediction is further reinforced by the observation that 7 of the high BP tracking adolescents had a definitive family history of hypertension. The higher proportion of males and the slightly higher BMI of subjects within the high BP tracking group, (both of which are characteristics of adult essential hypertension), is probably only a co-incidental finding in this study.

Cheek cells from adolescent subjects from each BP tracking group were assayed for Na$^+$ transport activity ($^{22}$Na$^+$ uptake) on the day of isolation using the methods fully described in Testing Method 3. FIG. 6 shows the total, control and net rates of Na$^+$ transport activity following a 2 minute assay time course for cheek cells from subjects within the two adolescent study groups. Both proton-dependent (total and net) and non-proton dependent (control) rates of Na$^+$ transport, are significantly reduced in cheek cells from subjects in the high BP tracking group. The extent of this reduction in cheek cell Na$^+$ transport activity (about 50% of the rate apparent for the low BP tracking group), equates with the extent of the difference evident between adult normotensive and hypertensive study groups (described in the previous section).

FIG. 7 shows the total, control and net rates of Na$^+$ transport activity following a 5 minute assay time course for cheek cells from subjects within the two adolescent study groups. As is the case for the 2 minute time point, both proton-dependent (total and net) and non-proton dependent (control) rams of Na$^+$ transport, are significantly reduced in cheek cells from subjects in the high BP tracking group. Again this equates with the extent of difference evident in the adult cheek cell study. The only distinction between the adult and adolescent studies thus far, is the difference in the rate of Na$^+$ transport activity in the control assay situation where the absence of a proton gradient would be expected not to activate Na$^+$/H$^+$ antiporter activity. In the adolescent study this difference does reach statistical significance. However a similar trend of lower (control) Na$^+$ transport activity in cheek cells from subjects in the adult hypertensive study group, is clearly apparent.

Figure 8A:
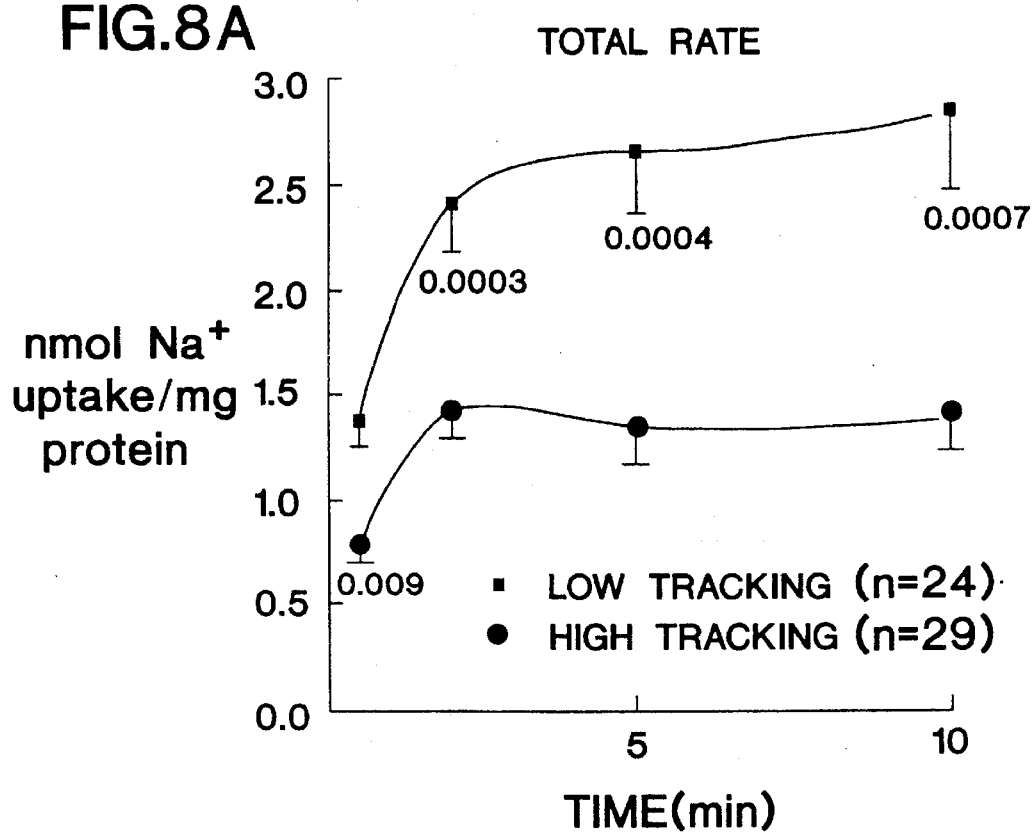
FIG. 8 illustrates time course for total and miloride sensitive sodium transport in cheek cells of low BP and high BP tracking adolescents. Proton dependent total and proton dependent amiloride sensitive rates of $^{22}Na^+$ uptake in cheek cells were determined at a proton gradient (inside→outside) of 100:1 over a period of 10 minutes as described in Testing Method 3.
Figure 8B:
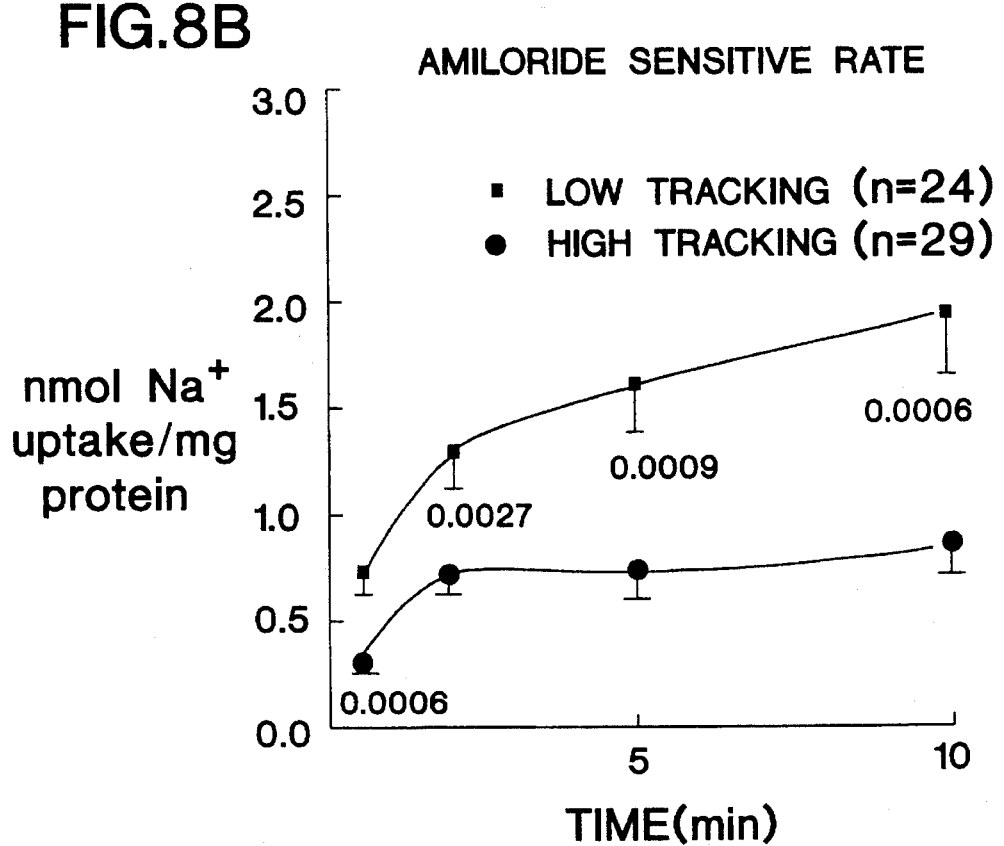

The effect of amiloride, a specific inhibitor of Na$^+$/H$^+$ antiporter activity, has also been tested in the adolescent study. The rationale for including this additional step in the assay protocol is to determine whether the amiloride sensitive Na$^+$ transport rate, which represents that component of Na$^+$ uptake dependent on the activity of the Na$^+$/H$^+$ antiporter, differs between the two adolescent study groups. FIG. 8 shows a time course for the total and the amiloride-sensitive rates of Na$^+$ transport in cheek cells from subjects in the low and high BP tracking groups. Both total and amiloride sensitive Na$^+$ transport activity in cheek cells from subjects in the high BP tracking group are significantly reduced in comparison to the low BP tracking group at all four time points examined.

This result further indicates that some property of the cheek cell Na$^+$/H$^+$ antiporter activity and/or its activation by a proton gradient, underlies the phenomenon observed in these studies. As was done in the adult study, the activation of the Na$^+$/H$^+$ antiporter system by a proton gradient has also been investigated in cheek cells obtained from the respective adolescent study groups. This was accomplished by comparing the response of the Na$^+$/H$^+$ antiporter system (and hence Na$^+$ uptake), to outwardly-directed proton gradients which differ in their magnitude.

Figure 9:
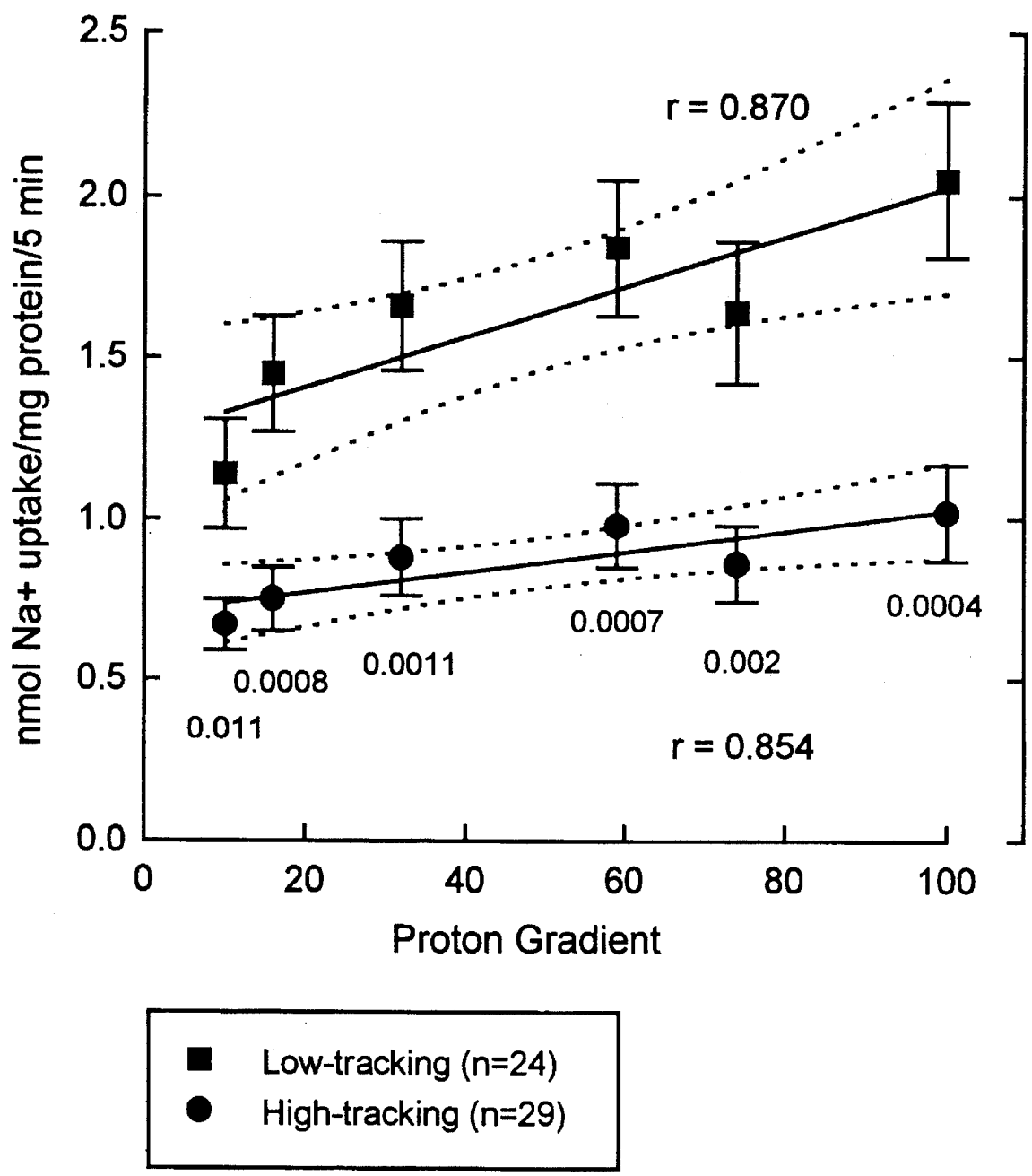
FIG. 9 illustrates the effect of altered proton gradient on the net rate of proton dependent sodium transport in cheek cells of low BP and high BP tracking adolescents. Net rates of proton dependent $^{22}Na^+$ transport (total minus control) at 5 minutes were determined at the indicated proton gradient (inside→outside) values as described in Testing Method 3. Values for the regression coefficient (r), and the 95% limites of confidence for each group are indicated.

The response of cheek cell proton-dependent sodium transport to proton gradients varying in magnitude from 10:1 to 100:1 (inside→outside) in low BP and high BP tracking adolescents is shown in FIG. 9. The rates of proton-dependent sodium transport in the high BP tracking adolescent group are markedly reduced at all proton gradient values as compared to the other adolescent study group. Furthermore, for the high BP tracking groups, the slope for the proton gradient activation of cheek cell Na$^+$ transport is markedly reduced over that obtained for the low BP tracking group.

The response of the cheek cell proton dependent sodium transport to a change in the magnitude of the proton gradient from 10:1 to 100:1, is shown in Table 4. These values represent the slope of the line between the abovementioned proton gradient values as depicted in FIG. 9. As can be seen from this table, the slope of the line between low and high BP tracking adolescent groups differs by a factor of 2.5 fold at a significance level of P=0.002; i.e. the mean increase in proton-dependent Na$^+$ transport is 2.5 times less in the high BP tracking adolescents as compared to the low BP tracking adolescents. However, the magnitude of this difference in the slope of the proton-dependent Na$^+$ transport between the adolescent study groups is nowhere near the 24 fold difference evident in the adult study. The fact that the magnitude of this difference in the adolescent study was "dampened" as compared to the adult study, may be a reflection of the different nature and composition of the two study groups in question.

Figure 10:
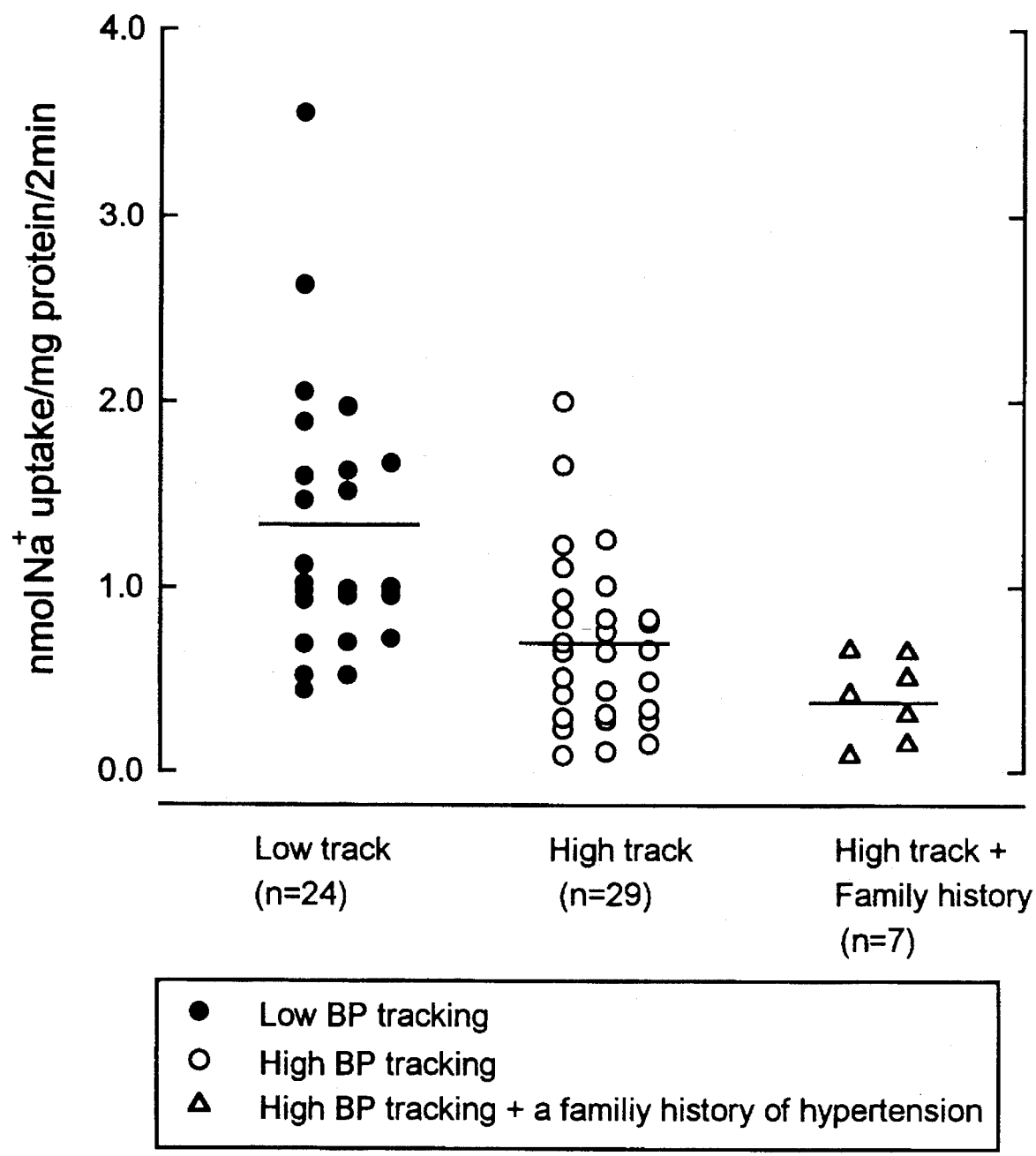
FIG. 10 illustrates sodium transport rates in cheek cells of individual low BP and high BP tracking adolescents, and high BP tracking adolescents with a family history of essential hypertension. Net rates of proton dependent $^{22}Na^+$ transport (total minus control) at 2 minutes incubation at a proton gradient (inside→outside) of 32:1 were determined as described in Testing Method 3.

FIG. 10 shows sodium transport rates (at a proton gradient value of 32:1) in cheek cells of individual low BP and high BP tracking adolescents, and high BP tracking adolescents with a family history of essential hypertension. Cheek cells from the high BP tracking group display a markedly reduced mean rate, (mean±SEM; 0.73±0.08 nmol $Na^+$.mg protein.5 min) of proton-dependent $Na^+$ transport which is 57% of the rate for the low BP tracking adolescents; (1.28±0.17 nmol $Na^+$.mg protein.5 min), and this difference is highly significant ($P=0.0032$; Student's unpaired t-test). The mean $Na^+$ transport rate for those 7 subjects in the high BP tracking groups (0.46±0.07 nmol $Na^+$.mg protein.5 min) is 63% when compared to the mean rate for the total high BP tracking adolescents, and 36%; ($P=0.016$) when compared to the mean rate for the low BP tracking adolescents.

TABLE 4

RESPONSE OF CHEEK CELL PROTON-DEPENDENT
SODIUM TRANSPORT TO A CHANGE
IN THE PROTON GRADIENT IN LOW BP TRACKING
AND HIGH BP TRACKING ADOLESCENT SUBJECTS

| Low tracking | n = 24 | 0.91 ± 0.15[1] | nmol $^{22}Na$ · mg protein · 5 min (for a change in the proton gradient from 10:1 to 100:1) |
|---|---|---|---|
| High tracking | n = 29 | 0.36 ± 0.09 | |
| Significance | | P = 0.002 | |

[1]Data is presented as the mean ± SEM for the indicated number of subjects (n) in each group. The significance of the difference between the mean was determined by Student's unpaired t-test.

The $Na^+$ transport rates of high BP tracking adolescents with a family history of hypertension are all below the mean value for $Na^+$ transport for the total high BP tracking group, and overlap with only 3 of the 24 subjects in the low BP tracking group.

It is therefore clearly apparent that those adolescents who display both a high BP tracking profile together with a family history of hypertension, also have the characteristic of a significantly and distinctly low rate of protons-dependent $Na^+$ transport activity in their cheek cells, and indeed can be distinguished by this latter characteristic. In this regard, the biochemical parameter under study in this embodiment, i.e. cheek cell $Na^+$ transport activity, displays similar characteristics in this group of adolescents (who may be considered at greatest risk of later developing hypertension) when compared to the group of hypertensive adults described in the previous section.

Figure 11:
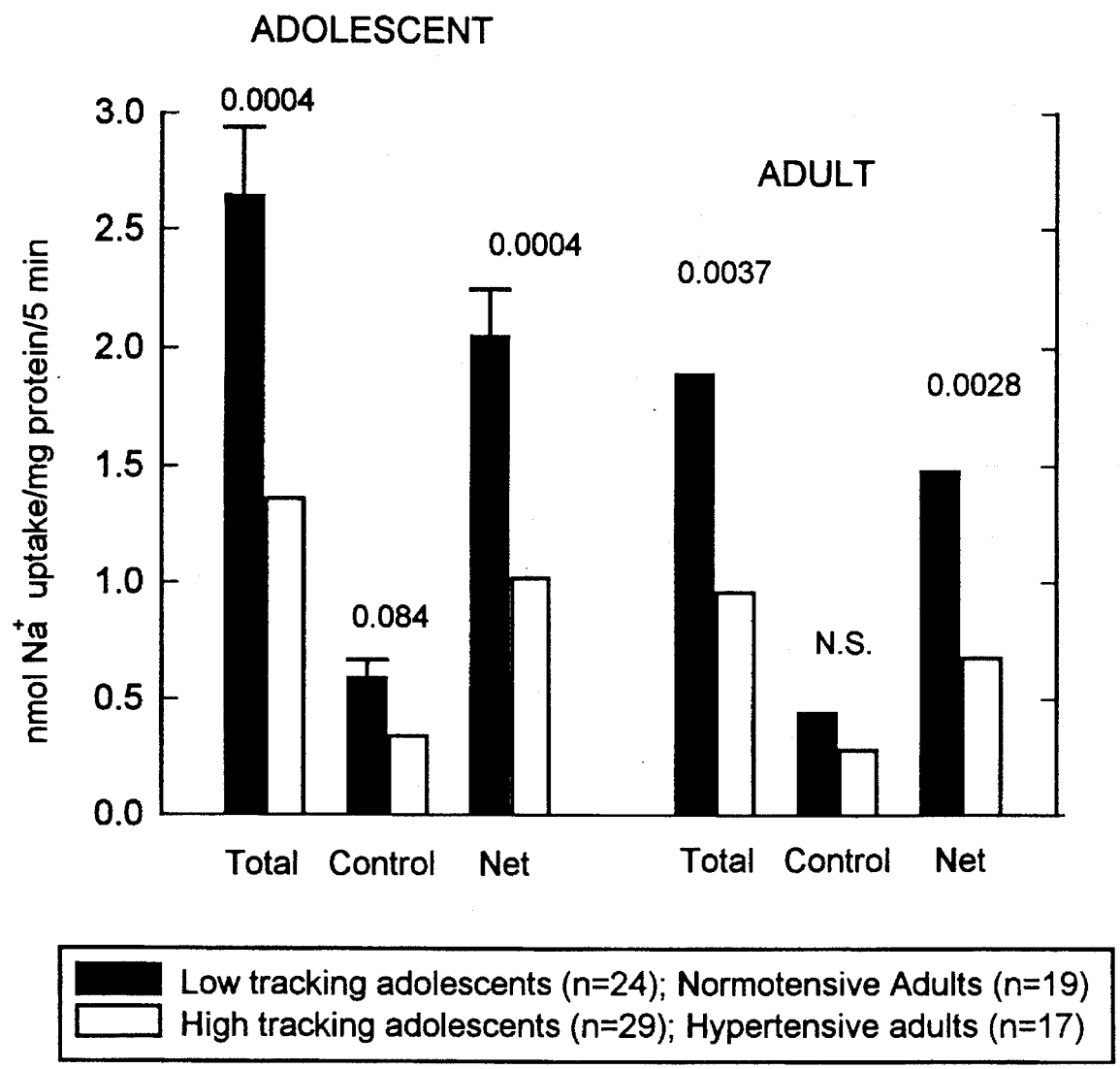
FIG. 11 illustrates comparison of sodium transport rates in cheek cells of low BP and high BP tracking adolescents, and normotensive and hypertensive adults. Proton dependent (total), non proton dependent (control) and net proton dependent (total minus control) rates of $^{22}Na^+$ uptake after 5 minutes incubation at a proton gradient (inside→outside) of 100:1 in cheek cells of low and high BP tracking adolescents and normotensive and hypertensive adults. Measurements of sodium transport were determined as described in Testing Methods 2 and 3.

Finally, a comparison is made between the sodium transport rates of cheek cells from the study groups within the adolescent and the adult studies. FIG. 11 shows the total, control and net rates of $Na^+$ transport in the adolescent and adult studies when examined after a 5 minute assay time course and a 100:1 outwardly-directed proton gradient. The extent of the difference between low BP and high BP tracking adolescents on the one hand, and between normotensive and hypertensive adults on the other, is striking for all three assay variations examined. Despite the fact that there was a six-month interval between these studies, with the adolescent study following after the adult study, the overall rates of cheek cell $Na^+$ transport activity are nevertheless very similar.

Discussion

A comparison of previous studies of cation transport in red blood cells, leucocytes and platelets of hypertensive and normotensive subjects with the present cheek cell assay for hypertension, is shown in Table 6. Twenty three other studies, most of which have used red blood cell $Li^+$—$Na^+$ countertransport activity to discriminate between hypertensive and normotensive subjects, are listed in this Table. For ease of comparison of these data with that of our own, some computational parameters have been calculated to allow both the extent of the difference between the normotensive and the hypertensive rates of cation transport ($H\bar{x}/N\bar{x}$) and the extent of overlap between the two groups, to be more readily compared; (these terms are defined in the legend to Table 6).

It is immediately apparent from our data on the adult hypertensive study that unlike the situation in all the other cited studies, the rate of proton-dependent sodium uptake is lower in hypertensive subjects when cheek cells are used for measurement. This contrasts with the six studies in which $Na^+/H^+$ antiporter activity has been measured in red blood cells, leucocytes and platelets. $Li^+$—$Na^+$ countertransport activity in red blood cells, which is most often measured as the rate of sodium-dependent lithium efflux, is more difficult to relate to the $Na^+/H^+$ antiporter of proton-dependent sodium transport. Nevertheless, in the studies shown, $Li^+$—$Na^+$ countertransport activity in red blood cells of hypertensive subjects is between 104% and 371% the rate observed with normotensive subjects and the significance of the difference between the two groups ranges from N.S. to $P<0.001$.

This same situation of decreased sodium transport activity is also apparent in the adolescent cheek cell study. For the adolescent study however, the extent of overlap has not been included or compared to the other studies shown in Table 6 for the previously stated reasons that the adolescent study groups are not directly comparable to the studies using adult hypertensive and normotensive subjects. FIG. 11 showing a comparison of cheek cell sodium transport activity between the adult and adolescent studies confirms the similarity of the two studies reported in this invention. When these combined results are viewed against the studies of others shown in Table 6, it is clear that the parameter measured in the cheek cell assay is behaving in a manner opposite to that reported by others (using other cell types) in relation to hypertension (and also the prehypertension situation).

The converse finding of a lower cation transport activity in the cheek cells of our hypertensive group, (and in the BP high tracking adolescent group with a family history of hypertension; the "prehypertensive group") is at present difficult to explain in the light of the findings from the cited studies. However, in this respect we have noted that cheek cells exhibit certain properties which differ significantly from those found in the other types of cells cited in Table 6. One example is the apparent inability of cheek cells to display significant osmotic behaviour as is the case for human red blood cells. This would suggest that a basic difference may exist in cell membrane permeability to ions and solutes in cheek cells as opposed to many other mammalian cell types.

It is therefore possible that some property unique to epithelial cells may account for our particular observation in relation to the hypertensive and normotensive groups as well as in the adolescent study. One likely explanation of our result is that the cheek cell plasma membrane of the adult hypertensive and the "prehypertensive" group, has a far greater permeability to protons ($H^+$) than is the case for the other two comparable study groups. This would imply that with the imposition of a proton gradient (inside→outside), less protons would be available to couple with the cell membrane located $Na^+/H^+$ antiporter due to increased loss of cytosolic protons through the cell membrane; hence the finding of a lower rate of proton-dependent sodium transport in these (hypertensive/prehypertensive) groups.

An increase in cheek cell membrane permeability to protons in the hypertensive and prehypertensive groups is borne out experimentally by examining the response of cheek cell sodium transport activity to proton gradients differing in their magnitude. It is clear from the data in FIGS. 4 and 9, and Tables 2 and 4, that the slope (or response) of sodium transport to an increasing proton gradient is significantly less in both the above study groups across the range of proton gradient values examined. This would indicate that an equivalent number of protons is either not present (via rapid dissipation due to increased membrane permeability), and/or that the extent of coupling of proton efflux to sodium uptake differs in the hypertensive (and prehypertensive) groups compared to their respective control groups.

Besides a difference in membrane proton permeability and/or proton coupling to the cheek cell $Na^+/H^+$ antiporter, yet another explanation for over result may lie in an enhanced permeability of the cell membrane to sodium ions, particularly in regard to the rate of efflux of $Na^+$ which has entered the cheek cell during the proton activation of the $Na^+/H^+$ antiporter. We have observed that efflux of $^{22}Na^+$ from cheek cells is a rapid event and that $Na^+$ efflux is probably occurring during the $Na^+$ uptake process, albeit at a rate less than the rate of $Na^+$ uptake during the fast 10 minutes of the assay incubation when measured at 25° C. A greater rate of efflux of transported $Na^+$ ions in the cheek cells of the hypertensive and prehypertensive groups compared to their respective control groups, could account for our experimental findings.

An important difference between the cheek cell assay method described herein and those studies of others referred to in Table 6, is the final concentrations of sodium ion ($Na^+$) used in the respective assays. In contrast to the studies listed in Table 6, all of which used a final concentration of about 150 mM $Na^+$ and did not rely on a radioisotopic technique for assay, the present invention uses a final concentration of 1 mM $Na^+$ containing 4.3 to 6.4 µCi (159–237 kBq) $^{22}Na^+$ per µmole $Na^+$. As has been previously mentioned in the section dealing with the characterisation of cheek cell $Na^+$ transport and $Na^+/H^+$ antiporter activity, a final concentration of 1 mM $Na^+$ is well below the Km value of $Na^+$ for the cheek cell $Na^+/H^+$ antiporter. As such, in our assay this transport system would be operating with $Na^+$ transport rates many times less than the maximum rate achievable if Michaelis-Menton kinetics were operative and the substrate ($Na^+$) was saturating. This is in direct contrast to the situation in the other studies listed in Table 6 in which the concentration of $Na^+$ in those assays would be saturating and the $Na^+/H^+$ antiporter would be operating at its maximum rate.

As a consequence of this important difference in the manner in which the sodium transport assays were carried out between this and the other cited studies, it would be expected that the respective assays would exhibit a differential sensitivity to those parameters which may affect the rate of sodium ion transport by the $Na^+/H^+$ antiporter. Thus, under saturating (high $Na^+$ assay concentration) conditions, differences in the absolute mount of $Na^+/H^+$ antiporter catalytic unit(s) present, may be more readily observable than would be the situation when substrate is limiting as is the case in the presently described cheek cell assay. On the other hand however, at low substrate ($Na^+$) concentrations where the activity of the $Na^+/H^+$ antiporter is well below its maximum rate, the influence of other factors, such as proton permeability may be more apparent. This may come about due to the fact that the outwardly-directed proton gradient is not being rapidly dissipated via the $Na^+/H^+$ antiporter because of the latter's relatively low activity. Dissipation of protons ($H^+$) could then occur via other mechanisms which may involve $H^+$ permeation through the cell membrane, and this rate of $H^+$ dissipation may represent an intrinsic and heritable characteristic of human essential hypertension. As such, the cheek cell assay method described herein may be inherently more sensitive to those biochemical factors which are perturbed in hypertension in comparison to the methods of others described in Table 6 which neither use cheek cells nor the assay techniques described in this invention.

In comparison to the studies cited in Table 6, it is clearly evident that for the adult cheek cell study, the difference in cation transport activity between normotensive and hypertensive subjects (irrespective of which group has the greater rate), exhibits the following:

(i) the greatest magnitude; $N\bar{x}/H\bar{x}=2400\%$ (ii) the greatest statistical significance; $P<0.0004$ (iii) the least overlap; 6%.

With reference to (iii): Overlap has been arbitrarily defined in Table 6 and data to calculate this parameter is only available in a limited number of studies. Attention is drawn to the Canessa study (Canessa et at., 1980) in which an overlap value of 0% was first reported. In their follow-up study (Semplicini et al., 1989) in which identical methods to the Canessa et al., (1980) study were employed, the overlap value averaged 26%.

The studies outlined in Table 6, particularly those in which $Na^+/H^+$ (rather than $Li^+$—$Na^+$) countertransport activities have been determined, do not show as great a difference between the two groups (141% to 195%) as found using the cheek cell assay method (293% to 2400%;$N\bar{x}/H\bar{x}$). This finding may be due to the fact that this present study was unique in that a range of proton gradient values were investigated with respect to proton-dependent sodium transport and that this present assay concentration of $Na^+$ was 1 mM.

Conclusions

It will be seen that the present invention is significant in that it achieves the following:

1) It allows the activity of a biochemical marker to be correlated with physiological disorders such as human hypertension in cheek cells which can be obtained in a relatively non-invasive manner.

2) It allows the potential for screening those people in the community who may be genetically predisposed to develop hypertension but are still in the prehypertensive state. Included in this category would be those adolescents who have high BP tracking characteristics and a family history of hypertension.

3) It is noted that this latter property is particularly significant in that for those who are identified as being in the prehypertensive stage, early measures could be taken to ameliorate later development of hypertension, or, at the very least, to minimise the extent of the hypertensive disorder.

This invention provides an assay which can be used to detect differences in the activity of a biochemical marker present in epithelial cells which can, with a minimum of overlap and with high statistical probability, discriminate between adult hypertensive and normotensive subjects, and between adolescents who have a family history of hypertension and high blood pressure tracking characteristics and those adolescents who do not. For the adult, the invention achieves a level of discrimination which is greater than any existing test done with cells derived from the blood of hypertensive subjects. For the adolescent, no such biochemical test has been described in the scientific literature to which the present invention can be compared.

Finally, it is clearly apparent from the examples given, that we have developed a technique which is far less invasive, and has greater discriminatory ability than all other tests so far described in the prior art.

Modifications to the Assay Method

The transport of sodium ions ($Na^+$) could also be measured using a fluorescent probe sensitive to small changes in $Na^+$ concentration in the cytoplasm of cheek cells resulting from $Na^+/H^+$ antiporter activity. Such a probe (SBFI/AM) is readily available commercially. The methodology for using this probe to measure changes in cytosolic $Na^+$ concentration in cells other than cheek cells, and in a variety of situations, has been described in the scientific literature.

Proton-dependent sodium transport and changes occurring in this parameter in association with hypertension, could also readily be measured by following the movement of protons ($H^+$) into and out of cheek cells. Movement of $H^+$ will result in changes in cheek cell cytosolic pH and this can also readily be measured by using a fluorescent probe sensitive to small changes in cytosolic pH in the cheek cell. Such a probe (BCECF/AM), together with a variety of other pH-sensitive probes, are also available commercially. Again, as for the $Na^+$ sensitive probe, there is comprehensive literature related to the general use of such fluorescent probes.

The fluorescent probe method(s) either singularly or in combination would greatly increase the speed at which assays could be done. They have the advantage over the radioisotopic method of providing a continuous reading of $Na^+$ and/or $H^+$ concentrations which would therefore turn the assay into a kinetic one. Measurements of proton-dependent sodium uptake (or sodium-dependent proton efflux) could be done using a suitable spectrofluorimeter which is available commercially. The assay may be designed in a manner similar to the radioisotopic method. Human cheek cells would be acidified by the methods described in this invention. The change in $Na^+$ concentration or cell pH ($H^+$ concentration), following the imposition of a suitable proton gradient, would be directly measured by following the change in the fluorescent spectra of the respective fluorescent probes(s). The above methodology could also be applied to directly measure the intrinsic $Na^+$ and $H^+$ permeability of the cheek cell to these ions. That is to say, that if the phenomenon described in this invention is explainable by an underlying biochemical mechanism involving an intrinsic difference in the permeability of the cheek cell membrane to these ions, then this permeability difference could also be measured. For example, in the final assay it may only be necessary to determine the response of the cytosolic pH of the cheek cell to changes in the external pH; i.e. to determine cytosolic buffering capacity in hypertensive and pre-hypertensive subjects. A fluorescent probe sensitive to cell pH such as BCECF/AM, could also be used in this regard.

It is also quite conceivable that the fluorescent probe method could subsequently be simplified to a far greater extent than described above. For example, the change in cheek cell $Na^+$ or pH ($H^+$) concentration could be detected at a single time point after the mixing of the reagents was completed. This may only involve a single point reading using a commonly available low-cost spectrofluorimeter.

Further streamlining the assay procedure described in this invention to reduce, cost, increase throughput and increase sensitivity, could easily be done by modifying the methods used in the assay of the biochemical marker as previously described. One such modification could be to rely on gamma counting as opposed to liquid scintillation counting as is done in the presently described invention. Sodium-22 has the following characteristics with regard to the emission of ionising radiation: $E\beta$, 0.546 Mev; $E\gamma$, 1.275 Mev. Gamma counting would make use of the relatively strong $\gamma$-ray emission and would negate the use of scintillation fluid in the counting step.

Another such modification would be to separate cheek cells from their uptake media using rapid centrifugation procedures in contrast to the rapid Millipore filtration method described in the present invention. Cheek cells could be spun out of their $^{22}Na^+$-containing uptake solutions using 1.5 ml Eppendoff centfifuge tubes loaded with an aliquot of a suitable density mix of phthalates into which cheek cells would migrate but the aqueous $^{22}Na^+$-containing uptake solutions would not.

As mentioned previously, the kit of the invention may include an appropriate mix of organic phthalates in a suitable container. The kit may also include a protocol for a centrifugation step to replace the Millipore filtration step in said assay procedure. Gamma counting can be used to replace beta liquid-scintillation counting.

Other Uses to which Human Cheek Epithelial (Buccal Mucosal) Cells have been Applied.

Although cheek cell scraping from the mouth is used extensively in teaching aspects of biology and cell structure in course work, to our knowledge their use in more applied scientific research did not occur until 1984. At that time the principal investigator concerned with the invention described herein, made use of human cheek cells to examine lipid profries in dietary and nutritional studies. These studies were reported in the following publications which have been fully listed in the bibliography. McMurchie et at., 1983; McMurchie et at., 1984a; McMurchie et at., 1984b; McMurchie et at., 1984c; Rohan et al., 1984; Margetts et al., 1985.

Since establishing the potential for human cheek cells to offer a relatively non-invasive source of tissue, a variety of different studies on cheek cells have appeared in the literature (it is stressed however, that to our knowledge, no studies concerning hypertension in general, or ion transport in particular, have appeared). These studies have been fully listed in the bibliography and include the following: Badcock et at., 1986; Tamai et al., 1988; Lench et at., 1988; Sampugna et al., 1988 and Wang et at., 1990.

In addition, the following articles have made reference to the use of cheek cells in nutritional studies: Relation of changes in dietary fatty acid to alterations in linoleic acid content of human cheek cell phospholipids. Editorial Review, Nutrition Reviews (1984), 42 376–377; (EJM work cited in references): Methods for obtaining fat microbiopsies. Editorial comment, *Nutrition Reviews* (1986), 44, 200–201; (EJM work cited in references).

Testing Method 1

Materials and methods for measuring the characteristics of sodium transport in human cheek cells.

Collection of cheek cells

Cheek (buccal mucosal) cells were obtained in a non-invasive manner by having subjects swish distilled water around their mouth for a short period of time, using a gentle molar scraping action. The expectorate containing the cheek cells was collected and a further two or three 10 ml washes produced an average total yield of about 4 million cells. Samples were spun at 46,000 g×15 minutes in a Beckman J2-21 centrifuge using a JA-20 rotor at 4° C. The packed cheek cell pellet was resuspended in 1 ml distilled water by gentle homogenisation. Cheek cells were isolated from subjects in the morning and assayed for $Na^+/H^+$ antiporter activity on the same day.

Measurement of $Na^+$ transport by the $Na^+/H^+$ antiporter assay $Na^+/H^+$ antiporter activity was measured by the uptake of $^{22}H^+$ using a modification of the Millipore filtration technique as described by Seiler et al., (1985). All cell equilibration and transport buffers used were prepared by titrating a pH 5.5, buffer: 230 mM mannitol, 49 mM MES, 11.2 mM N-methyl-D-glucamine (NMG), 1 mM ethyleneglycol-bis-(β-amino-ethyl ether)N,N'-tetra-acetic acid (EGTA), with a pH 8.4 buffer: 230 mM mannitol, 16.8 mM glycylglycine, 26.4 mM NMG, 1 mM EGTA, to produce buffers of differing pH value as required.

The cheek cell suspension was acidified at room temperature for 3 hours in approximately 20 volumes of pH 5.5 buffer (for proton-dependent and non proton-dependent $^{22}Na^+$ uptake) or in pH 7.8 buffer (for non proton-dependent $^{22}Na^+$ uptake).

Samples were centrifuged as described and resuspended in their respective buffers to give a final protein concentration of between 5 and 15 mg/ml plus or minus the addition of 1 mM ouabain, 1 mM bumetanide, or 1 mM amiloride and further incubated at 25° C. for 15 minutes.

The timed proton-dependent reaction was initiated at 25° C. by a ten-fold dilution of acidified (pH 5.5) cells into uptake buffer normally at pH 7.8 which gave a final pH in the assay of 7.5 and hence a transmembrane proton gradient (inside outside) of 100:1. Measurements were also made using uptake buffers of differing pH to produce a range of final proton gradients as indicated. Non proton-dependent sodium uptake was measured by adding cells loaded at pH 5.5 or pH 7.8 to buffer of the same pH. Uptake buffer for the 100:1 proton gradient contained a final concentration of 230 mM mannitol, 20.8 mM NMG, 18 mM MES, 10.7 mM glycylglycine, 1 mM EGTA, 1 mM $Na^+$(gluconate) and $^{22}Na^+$ ($Cl^-$) (carrier free) at 2×107 cpm/ml (6.4 uCi/ml), 500–1500 ug/ml cheek cell protein plus or minus 1 mM ouabain. $Na^+$ uptake was also measured in the presence of 1 mM amiloride.

The reaction was terminated at various times as indicated by adding 25 ul aliquots of the reaction mix to 4 ml ice-cold wash buffer containing 1 mM NaCl, 100 mM mannitol, 100 mM $MgCl_2$, 8 mM HEPES, 4 mM TRIS, pH 7.2. Cells containing $^{22}Na^+$ were collected by rapid filtration through 0.45 micron Millipore filters which were then washed twice with 4 ml ice-cold wash buffer. Filters were dried and covered with 4 mls Dupont Econofluor scintillant and counted in a Wallac 1410 beta-counter.

Measurements were made in duplicate or triplicate and background $^{22}Na^+$ retained on filters in the absence of cheek cells was subtracted from the assay values. Cheek cell protein was determined by the method of Lowry et al., (1951) and controlled for the background colour reading produced by NMG.

Rat kidney brash border membrane vesicles (BBMV) exhibiting high levels of proton-dependent $Na^+$ uptake were prepaxed according to the method of Hilden et al., (1989) using $Mg^{2+}$ aggregation with sequential centrifugation. $Na^+/H^+$ antiporter activity of BBMV was measured with every daily set of cheek cell assays as described above as a check on the assay procedure.

Cell counting and vital staining

Small aliquots of cells from the final pH 5.5 cell suspension were diluted in a congo red or trypan blue solution to give a final stain concentration of 0.06% (w/v). Cells were examined under an Olympus microscope at ×400 magnification using an Improved Neubauer haemocytometer. The cells were counted and inspected for their inclusion or exclusion of vital stain.

Chemicals

Amiloride HCL, bumetanide and ouabain were obtained from Sigma Chemical Co. All other reagents were of the highest commercial grade available.

Testing Method 2

Materials and methods for measuring sodium transport in the adult cheek cell study.

Subjects

Normotensive and hypertensive subjects were recruited from a total of 1100 adult male and female volunteers who participated in a blood pressure screening program. The hypertensive group comprised subjects having an average of their second and third sitting diastolic blood pressure readings of ≦95 mm Hg when measured with a Dinamap automatic blood pressure recorder and were aged between 25 and 60 years. The control group had a diastolic blood pressure of <85 mm Hg and were matched to the hypertensive group for age and gender. None of the control or hypertensive subjects selected for the final study were receiving antihypertensive medication at the time of the blood pressure screening or during the collection of cheek cells. On the same morning of cheek cell sampling, the blood pressure was re-measured to confirm previous readings. Characteristics of the respective study groups are shown in Table 1.

Collection of cheek cells

Cheek (buccal mucosal) cells were obtained in a non-invasive manner by having subjects swish distilled water around their mouth for a short period of time, using a gentle molar scraping action. The expectorate containing the cheek cells was collected and a further two or three 10 ml washes produced an average total yield of about 4 million cells. Samples were spun at 46,000 g×15 minutes in a Beckman J2-21 centrifuge using a JA-20 rotor at 4° C. The packed cheek cell pellet was resuspended in 1 ml distilled water by gentle homogenisation. Cheek cells were isolated from subjects in the morning and assayed for $Na^+/H^+$ antiporter activity on the same day. There was no significant difference between the cell yield of the normotensive group compared to the hypertensive group.

Measurement of $Na^+$ uptake by the $Na^+/H^+$ antiporter assay $Na^+/H^+$ antiporter activity was measured by the uptake of $^{22}Na^+$ using a modification of the Millipore filtration technique as described by Seiler et al.,(1985

700 ul of the cheek cell suspension was acidified at room temperature for 3 hours in 15 ml of Buffer I (pH 5.5) containing 230 mM mannitol, 49 mM MES, 11.2 mM N-methyl-D-glucamine (NMG), and 1 mM ethyleneglycol-bis-(β-amino-ethyl ether)N,N'-tetra-acetic acid (EGTA) (for proton-dependent and non proton-dependent $^{22}Na^+$ uptake). The remainder (300 ul) was equilibrated in 1.5 ml of Buffer II (pH 7.8) containing 230 mM mannitol, 33.6 mM HEPES, 26.4 mM NMG and 1 mM EGTA (for non proton-dependent $^{22}Na^+$ uptake). Samples were centrifuged as described above, and resuspended in their respective buffer plus the addition of 1 mM ouabain, and further incubated at 25° C. for 15 mins.

The timed proton-dependent reaction was initiated at 25° C. by a ten-fold dilution of pH 5.5 loaded cells (15 ul) into uptake buffer (150 ul final volume) consisting of Buffer II titrated with MES to pH values of 7.05, 7.35, 7.65 and 7.8. This provided final proton gradients (inside→outside) of 19:1, 40:1, 75:1 and 100:1, respectively. Non proton dependent $^{22}Na^+$ uptake was measured by adding cells loaded at pH 5.5 or pH 7.8 to uptake buffer of the same pH. For the 100:1 proton gradient, the reaction buffer contained a final concentration of 230 mM mannitol, 4.9 mM MES, 30.2 mM Hepes, 24.9 mM NMG, 1 mM EGTA, 1 mM $Na^+$ (gluconate) and $^{22}Na^+(Cl^-)$ (carrier free) at $13.3 \times 10^6$ cpm/ml (4.3 uCi/ml), 500–1500 ug/ml cheek cell protein, plus or minus 1 mM ouabain, pH 7.5. $Na^+$ uptake was also measured in the presence of 1 mM bumetanide.

The reaction was terminated at 30 seconds and 5 minutes by adding 25 ul aliquots of the reaction mix to 4 ml ice-cold wash buffer containing 1 mM NaCl, 100 mM mannitol, 100 mM $MgCl_2$, 8 mM HEPES, 4 mM TRIS, pH 7.2. Cells containing $^{22}Na^+$ were collected by rapid filtration through 0.45 micron Millipore filters which were then washed twice with 4 ml ice-cold wash buffer. Measurements were made in duplicate (30 seconds) and triplicate (5 min). Filters were dried and covered with 4 ml DuPont Econofluor scintillant and counted in a Wallac 1410 beta-counter. Background values for $^{22}Na^+$ retained on the filters in the absence of cheek cells were subtracted from the assay values. Cheek cell protein was determined by the method of Lowry et al., (1951) and controlled for the background reading produced by NMG.

As a control for variability, weekly checks of cheek cell $Na^+/H^+$ antiporter activity of cells from a small number of normotensive volunteers were made throughout the duration of the study. In addition, rat kidney brush border membrane vesicles exhibiting high levels of proton-dependent sodium uptake (prepared as described by Hilden et al., 1989) using $Mg^{2+}$ aggregation with sequential centrifugation, were included with every daily set of assays as a check on the assay procedure.

Cheek Cell counting and trypan blue staining

Small aliquots of cells were sampled from the final cell preparations at pH 5.5 and pH 7.8 and diluted ten-fold in distilled water. An aliquot of this dilution was added 1:1 with a neutral filtered aqueous 0.2% (w/v) trypan blue solution to give a final stain concentration of 0.1% (w/v). Cells were examined under an Olympus microscope at ×400 magnification using an Improved Neubauer haemacytometer that gave a viewing depth of 200 um. The cells were counted and inspected for their inclusion or exclusion of trypan blue.

Chemicals

Bumetanide and ouabain were obtained from Sigma Chemical Co. Sodium-22 was from New England Nuclear. All other reagents were of the highest commercial grade available.

Testing Method 3

Materials and methods for measuring sodium transport in the adolescent cheek cell study.

Subjects

Subjects were recruited from a 3-year blood pressure tracking study. Systolic and diastolic blood pressures were measured for 504 male and female high school students from two schools in 1986/87 and again in 1989/90. The setting up and actual running of these adolescent blood pressure surveys were carried out by Dr PRC Howe, CSIRO, Division of Human Nutrition, Adelaide, to whom we are most grateful. For both occasions, systolic blood pressure readings were regressed on age and age squared. Weight, height and obesity were not taken into account. Deviations of each student's observation-from the expected regression line were calculated, and from this each student was assigned a rank. The low BP and high BP tracking groups were identified from the upper and lower eight percent of the ranked sum of the two systolic blood pressure readings. Informed consent was obtained from 35 high and 32 low tracking adolescents. A final set of blood pressure readings in the seated position were taken using a Dinamap automatic blood pressure recorder on the day cheek cells were collected and sodium transport assayed. Characteristics of the study group are shown in Table 3. Six subjects from the high BP tracking group and eight subjects from the low BP tracking group recorded a final systolic blood pressure (on the day of cheek cell sampling) which was less than or greater than one standard deviation from the mean of their respective group. These subjects were not included in the final analyses.

Collection of cheek cells

Cheek Couccal) mucosal) cells were obtained in a non-invasive manner by having subjects swish distilled water around their mouth for a short period of time, using a gentle molar scraping action. The expectorate containing the cheek cells was collected and a further two or three 10 ml washes produced an average total yield of about 4 million cells. Samples were spun at 46,000 g×15 minutes in a Beckman J2-21 centrifuge using a JA-20 rotor at 4° C. The packed cheek cell pellet was resuspended by gentle homogenisation in loading buffer (pH 5.5) as described below. Cheek cells were isolated from subjects in the morning and assayed for $Na^+/H^+$ antiporter activity on the same day.

Measurement of $Na^+$ transport by the $Na^+/H^+$ antiporter assay $Na^+/H^+$ antiporter activity was measured by the uptake of $^{22}Na^+$ using a modification of the Millipore filtration technique as described by Seiler et at., (1985). All cell equilibration and transport buffers used were prepared by titrating a pH 5.5 buffer: 230 mM mannitol, 49 mM MES, 11.2 mM N-methyl-D-glucamine (NMG), 1 mM ethyleneglycol-bis-(β-amino-ethyl ether)N,N'-tetra-acetic acid (EGTA), with a pH 8.4 buffer: 230 mM mannitol, 16.8 mM glycylglycine, 26.4 mM NMG, 1 mM EGTA to produce buffers of differing pH value as required.

Cheek cells were acidified at room temperature for 3 hours in approximately 20 volumes of pH 5.5 loading buffer (for proton-dependent and non proton-dependent $^{22}Na^+$ uptake) or in pH 7.8 buffer (for non proton-dependent $^{22}Na^+$ uptake). Samples were centrifuged as described above, and resuspended in their respective buffers to give a final protein concentration between 5 and 15 mg/ml plus or minus the addition of 1 mM ouabain and/or 1 mM amiloride and further incubated at 25° C. for 15 mins.

The timed proton-dependent reaction was initiated at 25° C. by a ten-fold dilution of acidified (pH 5.5) cells into uptake buffer (150 ul final volume) normally at pH 7.8 to give a final assay pH of 7.5 and hence a transmembrane proton gradient (inside outside) of 100:1. Measurements were also made using uptake media of differing pH to produce a range of final proton gradients as indicated. Non proton-dependent sodium uptake was measured by adding cells loaded at pH 5.5 to buffer of the same pH. Uptake buffer for the 100:1 proton gradient contained a final concentration of 230 mM mannitol, 20.8 mM NMG, 18 mM MES, 10.7 mM glycylglycine, 1 mM EGTA, 1 mM $Na^+$(gluconate) and $^{22}Na^+(Cl^+)$ (carrier free) at $2 \times 10^7$ cpm/ml (6.4

μCi/ml), 500–1500 ug/ml cheek cell protein, plus or minus 1 mM ouabain. $Na^+$ uptake was also measured in the presence of 1 mM amiloride. The reaction was terminated at various times as indicated by adding 25 ul aliquots of the reaction mix to 4 ml ice-cold wash buffer containing 1 mM NaCl, 100 mM mannitol, 100 mM $MgCl_2$, 8 mM HEPES, 4 mM TRIS, pH 7.2. Cells containing $^{22}Na^+$ were collected by rapid filtration through 0.45 micron Millipore filters which were then washed twice with 4 ml ice-cold wash buffer. All measurements were made in duplicate (for 30 seconds and 10 minutes) or triplicate (for 2 and 5 minutes). Filters were dried and covered with 4 ml Dupont Econofluor scintillant and counted in a Wallac 1410 beta-counter.

Background values for $^{22}Na^+$ retained on the filters in the absence of cheek cells were subtracted from the assay values. Cheek cell protein was determined by the method of Lowry et al., (1951) and controlled for the background colour reading produced by NMG.

As a control for variability, weekly checks of cheek cell $Na^+/H^+$ antiporter activity from a small number of normotensive volunteers were made throughout the duration of the study. In addition, rat kidney brush border membrane vesicles exhibiting high levels of proton-dependent sodium uptake (prepared as described by Hilden et al., 1989) using $Mg^{2+}$ aggregation with sequential centrifugation, were included with every daily set of assays as a check on the assay procedure.

Chemicals

Amiloride HCL and ouabain were obtained from Sigma Chemical-Co. Sodium-22 was from New England Nuclear (Australia).

Satistical Method 4

All data are presented as the mean ± the standard error of the mean with the significance of differences between means for each assay condition/time point for the study groups, being determined by Student's unpaired t-test.

TABLE 5

SUMMARY OF $Na^+$TRANSPORT/UPTAKE ACTIVITY IN VARIOUS TISSUES

| AUTHOR | TISSUE/MEMBRANE | ASSAY TEMP (°C.) | $[Na^+]_o$ (mM) | $Na^+$UPTAKE (nmol/mg) t = 1·min | MAXIMUM |
|---|---|---|---|---|---|
| Frelin et al., 1984 | Rat heart cells | 37 | 3.0 | 5.0 | 20.0 |
| Pierce et al., 1990 | Rat heart sarcolemma | 37 | 0.05 | 0.03 | 0.3 |
| Meno et al., 1989 | Rabbit heart sarcolemma | 22 | 0.1 | 2.0 | 4.0 |
| Seiler et al., 1985 | Canine heart sarcolemma | 25 | 1.0 | 13.0 | 15.0 |
| Periyasamy et al., 1990 | Bovine heart sarcolemma | 22 | 1.0 | 13.0 | 15.0 |
| Zadunaisky et al., 1989 | Shark retinal epithelium | 15 | 0.5 | 0.6 | 0.7 |
| Ramaswamy et al., 1989 | Human ileal BBMV[1] | 23 | 1.0 | 5.5 | 5.5 |
| Orsenigo et al, 1990 | Rat jejunum basolateral membrane | 28 | 1.0: 60 | 1.0; 40 | 1.1; 40 |
| Moran et al., 1989 | Rat kidney cortex BBMV | 25 | 1.0 | 0.9 | 1.0 |
| " | Rat kidney medulla BBMV | 25 | 1.0 | 0.4 | 0.5 |
| Freiberg et al., 1982 | Rat kidney cortex BBMV | 20 | 1.0 | 0.5 | 5.0 |
| Morduchowicz et al., 1989 | WKY[2] kidney cortex BBMV | 21–23 | 1.0 | 2.1 | 2.3 |
| " | SHR[3] kidney cortex BBMV | 21–23 | 1.0 | 2.1 | 2.6 |
| McMurchie (This study) | Human cheek cells | | | | |
| | Adult-normotensive | 25 | 1.0 | | 1.4 |
| | -hypertensive | 25 | 1.0 | | 0.7 |
| | Adolescent-low tracking | 25 | 1.0 | 2.0 | 2.8 |
| | -high tracking | 25 | 1.0 | 1.1 | 1.4 |

[1]BBMV-Brush border membrane vesicles
[2]WKY-Wistar-Kyoto rat
[3]SHR-Spontaneously hypertensive rat

TABLE 6

COMPARISON OF PREVIOUS STUDIES ON CATION TRANSPORT IN RED BLOOD CELLS, LEUCOCYTES AND PLATELETS OF HYPERTENSIVE AND NORMOTENSIVE SUBJECTS WITH THE PRESENT CHEEK CELL MARKER FOR HUMAN HYPERTENSION

| STUDY | [1]Hn | Nn | [2]H̄x/N̄x (%) | [3]P | [4]N > H̄x(% H) | [5]H < N̄x (% H) | [6]OVERLAP |
|---|---|---|---|---|---|---|---|
| | | | $Li^+$—$Na^+$ Countertransport-red blood cells | | | | |
| Weder 1986 | 14 | 31 | 119% | <0.05 | — | — | — |
| Weinberger et al 1989 | 21 | 23 (whites) | 145% | <0.01 | — | — | — |
| Weinberger et al 1989 | 12 | 11 (blacks) | 196% | <0.01 | — | — | — |
| Carr et al 1990 | 13 | 23 | 148% | <0.01 | 3/23 (13%) | 3/13 (23%) | 18% |
| Yap et al 1989 | 50 | 30 | 104% | N.S. | — | — | — |
| Morgan et al 1988 | 9 | 12 | 371% | not given | — | — | — |
| Canessa et al 1980 | 36 | 26 | 229% | <0.001 | 0/36 (0%) | 0/36 (0%) | 0% |
| Semplicini et al 1989* | 41 | 21 | 133% | <0.05 | 4/21 (19%) | 14/41 (34%) | 26% |

TABLE 6-continued

COMPARISON OF PREVIOUS STUDIES ON CATION TRANSPORT IN RED BLOOD CELLS,
LEUCOCYTES AND PLATELETS OF HYPERTENSIVE AND NORMOTENSIVE SUBJECTS
WITH THE PRESENT CHEEK CELL MARKER FOR
HUMAN HYPERTENSION

| STUDY | [1]Hn | Nn | [2]H$\bar{x}$/N$\bar{x}$ (%) | [3]P | [4]N > H$\bar{x}$(% H) | [5]H < N$\bar{x}$ (% H) | [6]OVERLAP |
|---|---|---|---|---|---|---|---|
| Adragna et al 1982 | 22 | 16 | 176% | <0.001 | — | — | — |
| Woods et al 1982 | 16 | 9 | 206% | <0.001 | — | — | — |
| Canali et al 1981 | 58 | 46 | 132% | <0.001 | — | — | — |
| Cusi at al 1981 | 45 | 24 | 130% | <0.01 | — | — | — |
| Trevisan et al 1983 | 23 | 64 | 129% | <0.05 | — | — | — |
| Williams et al 1983 | 54 | 511 | 123% | <0.001 | — | — | — |
| Clegg et al 1982 | 75 | 39 | 189% | <0.001 | — | — | — |
| Weder et al 1984 | 29 | 57 | 137% | <0.05 | — | — | — |
| Wiley et al 1984 | 27 | 20 | 109% | N.S. | — | — | — |
| | | | $Na^+$—$H^+$ Countertransport-Red blood cell | | | | |
| Morgan et al 1988 | 9 | 21 | 169% | <0.005 | — | — | — |
| Semplicini et al 1989* | 41 | 21 | 172% | <0.01 | 2/21 (9%) | 11/41 (27%) | 18% |
| | | | $Na^+$—$H^+$ Countertransport-leucocyte | | | | |
| Ng et al 1989 | 17 | 17 | 141% | <0.05 | 0/17 (0%) | 4/17 (23%) | 11.5% |
| Ng et al 1990 | 16 | 20 | 154% | <0.001 | — | — | — |
| Wehling et al 1991 | 12 | 24 | 104% | <0.05 | 4/24 (17%) | 2/12 (17%) | 17% |
| | | | $Na^+$—$H^+$ Countertransport-platelets | | | | |
| Livne et al 1987 | 7 | 20 | 195% | <0.005 | — | [6]N < H$\bar{x}$ (% N) | [7]H > N$\bar{x}$ (% H) |
| | | | Cheek Cell proton-dependent $Na^+$ uptake (This study) | | | | |
| Proton gradient (75:1) | 15 | 19 | 34% [N$\bar{x}$/H$\bar{x}$ (%) 293%] | <0.0004 | 1/19 (5%) | 1/15 (7%) | 6% |
| Slope with proton gradient (19:1–75:1) | 15 | 19 | 4% [N$\bar{x}$/H$\bar{x}$ (%) 2400%] | <0.003 | 2/19 (10%) | 2/15 (13%) | 11.5% |

*The study by Semplicini et al 1989 had as its principal investigator M. Canessa and was a follow up study of the one done by Canessa et al 1980.
[1]Hn and Nn refers to the number of hypertensives (H) and normotensives (N) in each study.
[2]H$\bar{x}$/N$\bar{x}$ (%) refers to the percentage increase (or decrease) between the mean rate of cation transport in the system under investigation in hypertensives (Hx) and normotensives (Nx).
[3]Probability that differences between groups were significant as determined by the statistical treatment used in each study. N.S., not significant.
[4]Number (%) of normotensives having a value greater than the mean of the hypertensive group.
[5]Number (%) of hypertensives having a value less than that the mean of the normotensive group.
[6]Number (%) of normotensives having a value less than that the mean of the hypertensive group.
[7]Number (%) of hypertensives having a value greater than the mean of the normotensive group.
[8]Average of (4) and (5) or (6) and (7).

REFERENCES

Adragna N. C., Canessa M. L., Solomon H., Slater E. and Tosteson D. C. (1982) Red cell $Li^+$/$Na^+$ exchange in patients with essential hypertension. *Hypertension* 4, 795–804.

Badcock N. R., O'Reilly D. A. and Pinmock C. B. (1986) Liquid chromatographic determination of retinal and α-tocopheml in human buccal mucosal cells. *J Chromatography* 382 290–296.

Canali M., Borghi L., Sani E., Cuff A., Montanari A., Novarini A., and Borghetti A. (1981) Increased erythrocyte lithium-sodium countertransport in essential hypertension: its relationship to family history of hypertension. *Clin. Sci.* (Suppl 7)61, 13s–15s.

Canessa M., Adragna N., Solomon H. S., Connolly B. S, and Tosteson D. C. (1980) Increased sodium-lithium countertransport in red cells of patients with essential hypertension. *N. Engl. J. Med.* 302, 772–776.

Carr S. J., Thomas T. H., Laker M. F., and Wilkinson R. (1990) Elevated sodium-lithium countertransport: a familial marker of hyperlipidaemia and hypertension! *J. Hypertension* 8, 139–146.

Clegg G., Morgan D. B., and Davidson C. (1982) The heterogeneity of essential hypertension. Relation between lithium efflux and sodium content of erythrocytes and a family history of hypertension. *Lancet* 2, 891–894.

Cusi D., Barlassina C., Ferrandi M., Palazzi P., Celege E. and Bianchi G. (1981) Relationship between altered $Na^+$-$K^+$ co-transport and $Na^+$-$Li^+$ countertransport in the erythrocytes of "essential" hypertensive patients. *Clin. Sci.* (Suppl I) 61, 33s–36s.

Freiberg J. M., Kinsella J. and Sacktor B. (1982) Glucoconicoids increase the $Na^+$/$H^+$ exchange and decrease the $Na^+$ gradient-dependent phosphate-uptake systems in renal brash border membrane vesicles. *Proc. Natl. Acad. Sci.* 79, 4932–4936.

Frelin C., Vigne P. and Lazdunksi M. (1984) The role of the $Na^+$/$H^+$ exchange system in cardiac cells in relation to the control of the internal $Na^+$ concentration. *J. Biol. Chem.* 259, 8880–8885.

Garay R. P. (1987) Kinetic aspects of red blood cell sodium transport systems in essential hypertension. *Hypertension* (Suppl. I) 10 I-11–I-14.

Hilden S. A., Johns C. A. and Madias N. E. (1989) Adaptation of robbit renal conical $Na^+$/$H^+$ exchange activity in chronic hypocapnia. *Am. J. Physiol.* 257 F615–F622.

Kneisley J., Schork N. and Julius S. (1990) Predictors of blood pressure and hypertension in Tecumseh, Michigan. *Clin. and Exper. Hyper.—Theory and Practice.* A12(5), 693–708.

Lench N., Stainer P. and Williamson R. (1988) Simple non-invasive method to obtain DNA for gene analysis. *Lancet* i, 1356–1358.

Livne A., Balfe J. W., Veitch R., Marquez-Julio A., Grinstein S. and Rothstein A. (1987) Increased platelet $Na^+$-$H^+$ exchange rates in essential hypertension: Application of a novel test. *Lancet* 1, 533–536.

Lowry O. H., Rosebrough N. J., Farr A. L. and Randall R. (1951) Protein measurements with the Folin phenol reagent. *J. Bid. Chem.* 193, 265–275.

Margetts B. M., Beilin L. J., Armstrong B. K., Rouse I. K., Vandongen R., Croft K. D. and McMurchie E. J. (1985). Blood pressure and dietary polyunsaturated and saturated fats: A controlled trial. *Clin. Sci.* 69 165–175.

Meno H., Jarmakani J. M. and Philipson K. D. (1989) Developmental changes of sarcolemmal $Na^+$-$H^+$ exchange. *Mol. Cell. Cardid.* 21, 1179–1185.

McMurchie E. J., Margetts B. M., Potter J. D., Armstrong B. K. and Hetzel B. S. (1983). The use of human cheek cells in dietary lipid studies. *Proc. Nut. Soc. of Aust.*, 8, 169–172.

McMurchie E. J., Potter J. D., Rohan T. E. and Hetzel B. S. (1984a) Human cheek cells: a non-invasive method for determining tissue lipid profiles in dietary and nutritional studies. *Nut. Rep. Internat.* 29 519–526.

McMurchie E. J., Margeits B. M., Beilin L. J., Croft K., Vandongen R. and Armstrong B. K. (1984b) Dietary-induced changes in the fatty acid composition of human cheek cell phospholipids: Correlation with changes in the dietary polyunsaturated/saturated fat ratio. *Am. J. Clin. Nut.* 39 975–980.

McMurchie E. J., Rohan T. E., Potter J. D., Margetts B. H. and Hetzel B. S. (1984c). Human cheek cells: their use in dietary lipid studies. *Comm. Health Sci.* 8 272.

Moran A., Stange G. and Murer H. (1989). Sodium-hydrogen exchange system in brush border membranes from cortical and medullary regions of the proximal tubules. *Blochem. Biophys. Res. Comm.* 163, 269–275.

Morduchowicz, G. A., Sheikh-Hamad D., Jo O. D., Nord E. P., Lee D. B. N. and Yanagawa N. (1989) Increased $Na^+/H^+$ antiport activity in the renal brash border membrane of SHR. *Kidney Int.* 36,576–581.

Morgan K., Canessa M., Goldzer R., Moore T. J. and Williams G. H. (1988) Red cell $Na^+/H^+$ exchange has a defective $H^+$ regulatory site in hypertensive patients with elevated $Li^+/Na^+$ exchange. *Clin. Res.* 36, 430 (Abstract)

Ng L. L., Dudley C., Bomford J. and Hawley D. (1989) Leucocyte intraceHular Ph and $Na^+/H^+$ antiport activity in human hypertension. *J. Hypertension* 7, 471–475.

Ng L. L., Fennell D. A. and Dudley C. (1990) Kinetics of the human leucocyte $Na^+$-$H^+$ antiport in essential hypertension. *J. Hypertension* 8, 533–537

Orsenigo M. N., Tosco M., Zoppi S. and Faelli A. (1990) Characterization of basolateral membrane Na/H antiport in rat jejunum. *BBA* 1062, 64–68.

Periyasamy S. M., Kakar S. S., Garlid K. D. and Askaft A. (1990) Ion specificity of cardiac sarcolemmal $Na^+/H^+$ antiporter. *J. Bid. Chem.* 256, 6035–6041.

Pierce G. N., Ramjiawan B., Dhalla N. S. and Feffari R. (1990). $Na^+$-$H^+$ exchange in cardiac sarcolemmal vesicles isolated from diabetic rats. *Am. J. Physiol.* (Heart Circ. Physiol. 27), 258 H255–H261.

Ramaswamy K., Harig J. M. Kleinman J. G. Harris M. S. and Barry J. A. (1989) Sodium-proton exchange in human ileal brash-border membrane vesicles. *BBA* 981, 193–199.

Rohan T., Belling G. B., McMurchie E. J., Cook M. G. and Hetzel B. S. (1984). A comparidon of dietary lipid intake with buccal cell and tissue lipid content. *Int Epidemiol. Assoc.* 10th Meeting, Vancouver, Abstract no. 324.

Sampugna J., Light L., Enig M. G., Jones D. Y., Judd J. T. and Lanza E. (1988). Cheek cell fatty acids as indicators of dietary lipids in humans. *Lipids* 23, 131–136.

Seiler S. M., Cragoe E. J. Jr., and Jones L. R. (1985) Demonstration of a $Na^+/H^+$ exchange activity in puffted canine cardiac sarcolemmal vesicles. *J. Bid. Chem.* 260, 4869–4876.

Semplicini A., Canessa M., Mozatto M. G., Ceolotto G., Marzola M., Buzzaccarini F., Casolino P. and Pessina A. C. (1989) Red blood cell $Na^+/H^+$ and $Li^+/Na^+$ exchange in patients with essential hypertension. *Am. J. Hypertens.* 2, 903–908.

Tamal H., Manago M., Yokota K., Kitagawa M. and Mino M. (1988) Determination of α-tocopherol in buccal mucosal cells using an electrochemical detector. *Internat. J. Vit. Nutr. Res.* 58, 202–207.

Trevisan M., Ostrow D., Cooper R., Liu K., Sparks S., Okonek A., Stevens E., Marquardt J. and Stander J. (1983) Abnormal red blood cell ion transport and hypertension: The People's Gas Company Study. *Hypertension* 5, 363–367.

Wang S-L., Mills M., Wu-Wang C. Y., Slomiany A. and Slomiany B. L. (1990). Identification of epidermal growth factor receptor in human buccal mucosa. *FASEB Abstracts Part 1.4*, A324.

Weder A. B., Torretti B. A. and Julius S. (1984) Radical differences in erythrocyte cation transport. *Hypertension* 6, 116–123.

Weder A. B. (1986) Red-cell lithium-sodium countertransport and renal lithium clearance in hypertension. *N. Engl. J. Med.* 314, 198–201.

Webling M., Käsmayr J. and Theisen K. (1991). The $Na^+/H^+$ exchanger is stimulated and cell volume increased in lymphocytes from patients with essential hypertension. *J. Hypertension.* 5, 519–524.

Weinberger M. H., Smith J. B., Fineberg N. S. and Luff F. C. (1989) Red-cell sodium-lithium countertransport and fractional excretion of lithium in normal and hypertensive humans. *Hypertension* 13, 206–212.

Wiley J. S., Clarke D. A., Bonaquisto L. A., Scarlett I. D., Harrap S. B., and Doyle A. E. (1984) Erythrocyte cation cotransport and countertransport in essential hypertension. *Hypertension* 6, 360–368.

Williams R. R., Hunt S. C., Hasstedt S. I., Hopkins P. N., Wu L. L., Berry T. D., Stults B. M., Barlow G. K., Schumacher M. C., Lifton R. P. and Lalouel J. M. (1990a). Multigenic human hypertension: evidence for subtypes and hope for haplotypes. *J. Hypertension* 8 (suppl 7): S39–S46.

Williams R. R., Hunt S. C., Hasstedt S. J., Hopkins P. N., Wu L. L., Berry T. D., Stults B. M., Barlow G. K. and Kuida H. (1990b). Genetics of hypertension: what we know and don't know. *Clin. and Exper. Hyper.—Theory and Practice* A12(5), 865–876.

Williams R. R., Hunt S. C., Kuida H., Smith I. B. and Ash K. O. (1983) Sodium-lithium countertransport in erythrocytes of hypertension prone families in Utah. *Am J. Epidemiol* 118, 338–344.

Woods J. W., Falk, F. J., Pittman A. W., Klemmer P. J. Watson B. S., and Namoordiri D. (1982) Increased red-cell sodium-lithium countertransport in normotensive sons of hypertensive parents. *N. Engl. J. Med.* 306, 593–595.

Yap L., Arrazola A., Soria F. and Diez J. (1989) Is there increased cardiovascular risk in essential hypertensive patients with abnormal kinetics of red blood cell sodium-lithium countertransport? *J. Hypertension* 7, 667–673.

Zadunaisky J. A., Kinne-Saffran E. and Kinn R. (1989) A Na/H exchange mechanism in apical membrane vesicles of the retinal pigment epithelium. *Invest. Opthal. & Vis. Sci.* 30, 2332–2340.

I claim:

1. A method for determining the presence of hypertension or a pre-disposition towards hypertension in a human subject, which method comprises:

determining the sodium ion ($Na^+$) uptake under an imposed proton ($H^+$) concentration gradient across the membrane of isolated single cheek epithelial (buccal mucosal) cells taken from said subject, wherein the rate of proton dependent sodium ion uptake by said cells indicates the presence of hypertension or a predisposition towards hypertension in said subject.

2. The method of claim 1, wherein the proton ($H^+$) concentration gradient across the cell membrane, from the inside to the outside, is in the range of about 10:1 to about 100:1.

3. The method of claim 2, wherein the proton ($H^+$) concentration gradient is about 75:1.

4. The method of claim 2, wherein the determination is carried out at two or more proton concentration gradients.

5. The method of claim 1, wherein the cell is exposed to a medium containing a $Na^+$ concentration in the range of 50 micromole to 150 millimole per liter.

6. The method of claim 5, wherein the $Na^+$ concentration is about 1 millimole per liter.

7. The method of claim 1, wherein the determination is carried out in the presence of an ($Na^+$–$K^+$)ATPase inhibitor.

8. The method of claim 7, wherein the inhibitor is ouabain.

9. The method of claim 1, wherein the sodium ion uptake is determined over a period ranging from about 15 seconds to about 40 minutes during incubation at about 25° C.

10. The method of claim 9, wherein the sodium ion uptake is determined over a period of 15 seconds to 10 minutes.

11. The method of claim 1, wherein the sodium ion uptake is measured by determining cell uptake of radioactively labelled $Na^+$.

12. The method of claim 1, wherein $Na^+$ or $H^+$ are measured using an ion specific fluorescent probe.

13. A method for determining the presence of hypertension or a pre-disposition towards hypertension in a human subject, said method comprising the steps of:

(a) establishing a proton ($H^+$) concentration across the membrane of cheek epithelial (buccal mucosal) cells taken from said subject, the proton concentration being greater inside said cells than outside said cells, by performing the substeps of:
 (i) incubating a sample of said epithelial cells taken from the subject in a first acidic medium,
 (ii) contacting the acidified cells from substep (i) with a second less acidic medium containing sodium ions ($Na^+$), and
 (iii) separating the cells from the second less acidic medium; and (b) determining the proton-dependent uptake of sodium ions ($Na^+$) by said cells when said cells are exposed to a medium containing sodium ions ($Na^+$), wherein the rate of proton dependent sodium ion uptake by said cells indicates the presence of hypertension or a predisposition towards hypertension in said subject.

14. The method of claim 13, wherein the proton ($H^+$) concentration gradient across the cell membrane, from the inside to the outside, is in the range of about 10:1 to about 100:1.

15. The method of claim 14 wherein the proton concentration gradient is about 75:1.

16. The method of claim 14 wherein the determination is carried out at two or more proton concentration gradients.

17. The method of claim 13 wherein the cell is exposed to a medium containing a $Na^+$ concentration in the range of 50 micromole to 150 millimole per liter.

18. The method of claim 17 wherein the $Na^+$ concentration is about 1 millimole per liter.

19. The method of claim 13 wherein the determination is carried out in the presence of an ($Na^+$+$K^+$)ATPase inhibitor.

20. The method of claim 19 wherein the inhibitor is ouabain.

21. The method of claim 13 wherein the $Na^+$ uptake is determined over a period ranging from about 15 seconds to about 40 minutes during incubation at about 25° C.

22. The method of claim 21, wherein the $Na^+$ uptake is determined over a period of 15 seconds to 10 minutes.

23. The method of claim 13 wherein $Na^+$ uptake is measured by determining cell uptake of radioactively labelled $Na^+$.

24. The method of claim 13 wherein $Na^+$ $H^+$ are measured using an ion specific fluorescent probe.

25. The method of claim 13 when used for the determination of hypertension in an adult.

26. The method of claim 13 when used for the determination of a predisposition to hypertension in said human subject.

27. The method of claim 13, which comprises the steps of:
(i) incubating a sample of said epithelial cells taken from the human subject in the first acidic medium, with said first acidic medium having a pH of 5.5 or higher;
(ii) contacting the so acidified cells with the second less acidic medium containing said sodium ions ($Na^+$), with said second acidic medium having a pH of 7.8 or lower;
(iii) separating the cells from the second less acidic medium; and
(iv) determining the uptake of said sodium ions ($Na^+$) by the cells.

28. An assay kit which is useful in a method for determining the presence of hypertension or a predisposition to hypertension in a human subject, the kit comprising:

a first acidic medium having a pH of 5.5 or higher in a suitable container for acidifying epithelial cells isolated from a human subject;

a second less acidic medium having a pH of 7.8 or lower containing sodium ions ($Na^+$) in a suitable container;

a third medium containing a final sodium ion ($Na^+$) concentration therein of from 50 micromoles to 150 millimoles per liter in a suitable container;

an indicator for the detection of sodium ion ($Na^+$) in a suitable container; and an inhibitor of ($Na^+$+$K^+$) ATPase activity in a suitable container.

29. The assay kit according to claim 28, wherein said epithelial cells are isolated single cheek epithelial (buccal mucosal) cells.

30. The assay kit according to claim 28, wherein the final sodium ion ($Na^+$) concentration in said third medium is about 1 millimole per liter.

31. The assay kit according to claim 28, wherein the indicator for sodium ion ($Na^+$) concentration is an ion specific fluorescent probe specific for Na$^+$, or H$^+$, or Na$^+$ and H$^+$.

32. The assay kit according to claim 28, wherein the inhibitor of (Na$^+$+K$^+$) ATPase activity is ouabain.

33. The assay kit according to claim 28, further comprising a predetermined mix of organic phthalates in a suitable container.

34. The assay kit according to claim 28, further comprising radioactive sodium ion (Na$^+$) in a suitable container.

35. The assay kit according to claim 29, wherein the final sodium ion (Na$^+$) concentration in said third medium is about 1 millimole per liter.

36. The assay kit according to claim 29, wherein the indicator for sodium ion (Na$^+$) concentration is an ion specific fluorescent probe specific for Na$^+$, or H$^+$, or Na$^+$ and H$^+$.

37. The assay kit according to claim 29, wherein the inhibitor of (Na$^+$+K$^+$) ATPase activity is ouabain.

38. The assay kit according to claim 29, further comprising a predetermined mix of organic phthalates in a suitable container.

39. The assay kit according to claim 29, further comprising radioactive sodium ion (Na$^+$) in a suitable container.

* * * * *